US012773111B2

(12) United States Patent
Cima et al.

(10) Patent No.: US 12,773,111 B2
(45) Date of Patent: Oct. 27, 2026

(54) METHODS OF FLUID ASSESSMENT AND TREATMENT

(71) Applicants: Massachusetts Institute of Technology, Cambridge, MA (US); The General Hospital Corporation, Boston, MA (US)

(72) Inventors: Michael J. Cima, Winchester, MA (US); Matthew Li, Somerville, MA (US); Lina Colucci, Austin, TX (US); Herbert Lin, Boston, MA (US); Kristin Corapi, Acton, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 1032 days.

(21) Appl. No.: 16/858,197

(22) Filed: Apr. 24, 2020

(65) Prior Publication Data

US 2020/0383574 A1 Dec. 10, 2020

Related U.S. Application Data

(60) Provisional application No. 62/837,954, filed on Apr. 24, 2019.

(51) Int. Cl.

*A61B 5/00* (2006.01)
*A61B 5/02* (2006.01)
(Continued)

(52) U.S. Cl.

CPC ............ *A61B 5/0036* (2018.08); *A61B 5/004* (2013.01); *A61B 5/02042* (2013.01);
(Continued)

(58) Field of Classification Search

CPC ... A61B 5/0036; A61B 5/004; A61B 5/02042; A61B 5/055; A61B 5/201; A61B 5/4842;
(Continued)

(56) References Cited

U.S. PATENT DOCUMENTS

| | | | | |
|---|---|---|---|---|
| 2016/0120438 A1* | 5/2016 | Cima | ........................ | A61B 5/02 600/410 |
| 2017/0325710 A1* | 11/2017 | Ryan | ........................ | A61B 5/055 |
| 2018/0306879 A1* | 10/2018 | Bashyam | ............. | G01R 33/383 |

OTHER PUBLICATIONS

Ababneh, Z., et al. (2005). Biexponential parameterization of diffusion and T2 relaxation decay curves in a rat muscle edema model : decay curve components and water compartments. Magnetic resonance in medicine, 54(3), 524-531. (Year: 2005).*
Araujo, E. C., et al. (2014). New insights on human skeletal muscle tissue compartments revealed by in vivo t2 NMR relaxometry. Biophysical journal, 106(10), 2267-2274. (Year: 2014).*
Sinclair, C. D., et al. (2016). Stability and sensitivity of water T2 obtained with IDEAL-CPMG in healthy and fat-infiltrated skeletal muscle. NMR in biomedicine, 29(12), 1800-1812. (Year: 2016).*
(Continued)

*Primary Examiner* — Michael J Carey
*Assistant Examiner* — Maria Christina Talty
(74) *Attorney, Agent, or Firm* — Eversheds Sutherland (US) LLP

(57) ABSTRACT

Methods of fluid assessment and treatment, which may include measuring a quantitative relaxation time (T2) of a muscle of a patient to determine whether the patient is hypovolemic, euvolemic, or hypervolemic. Methods of treatment may include determining a first fluid status of a patient by measuring a first quantitative relaxation time (T2) of a muscle of the patient, and administering to the patient a fluid reduction treatment or a hydration treatment.

18 Claims, 14 Drawing Sheets

(51) Int. Cl.

| | |
|---|---|
| ***A61B 5/055*** | (2006.01) |
| ***A61B 5/20*** | (2006.01) |
| ***A61M 1/16*** | (2006.01) |
| ***A61M 1/34*** | (2006.01) |
| ***A61M 5/14*** | (2006.01) |
| ***A61M 31/00*** | (2006.01) |

(52) U.S. Cl.

CPC .............. *A61B 5/055* (2013.01); *A61B 5/201* (2013.01); *A61B 5/4842* (2013.01); *A61B 5/4875* (2013.01); *A61B 5/4881* (2013.01); *A61M 1/16* (2013.01); *A61M 1/3417* (2014.02); *A61M 5/14* (2013.01); *A61M 31/00* (2013.01)

(58) Field of Classification Search

CPC ...... A61B 5/4875; A61B 5/4881; A61M 1/16; A61M 1/3417; A61M 5/14; A61M 31/00

See application file for complete search history.

(56) References Cited

OTHER PUBLICATIONS

Gerhalter, T., et al. (2017). Acute changes in extracellular vol. fraction in skeletal muscle monitored by 23Na NMR spectroscopy . Physiological reports, 5(16), e13380. (Year: 2017).*

Ericky C. A. Aruajo et al., "New Insights on Human Skeletal Muscle Tissue Compartments Revealed by In Vivo T2 NMR Relaxometry," Biophysical Journal, May 2014, vol. 106, pp. 2267-2274 (Year: 2014).*

Araujo, et al., "New Insights on Human Skelatal Muscle Tissue Compartments Revealed by In Vivo T2 NMR Relaxometry," Biophysical Journal, vol. 106, No. 10, May 21, 2014 (pp. 2267-2274).

Ababneh, et al., "Biexponential parameterization of diffusion and Ts relaxation decay curves in a rat muscle edema model: Decay curve components and water compartments," Magnetic Resonance in Medicine, vol. 54, No. 3, Sep. 1, 2005 (pp. 524-531).

International Application No. PCT/US2020/029903, Search Report and Written Opinion, mailed Oct. 14, 2020 (17 pages).

* cited by examiner

METHODS OF FLUID ASSESSMENT AND TREATMENT

CROSS-REFERENCE TO RELATED APPLICATIONS

This application claims priority to U.S. provisional patent application No. 62/837,954, filed Apr. 24, 2019, which is incorporated herein by reference.

STATEMENT REGARDING FEDERALLY SPONSORED RESEARCH AND DEVELOPMENT

This invention was made with Government support under Grant No. W911NF-13-D-0001 awarded by the Army Research Office (ARO). The Government has certain rights in the invention.

BACKGROUND

End-stage renal disease (ESRD) is typically associated with shortened life expectancy, despite intensive treatments such as hemodialysis (HD). The kidneys can play an integral role in maintaining euvolemia, and patients with ESRD, even those who undergo thrice weekly HD for the purposes of removing toxins and excess fluid, are often plagued by chronic volume overload.

In many instances, under-estimates of the fluid removal target during hemodialysis leave ESRD patients prone to chronic volume overload, hypertension, heart failure, or a combination thereof. Meanwhile, excessive fluid removal can lead to hypotension, muscle cramping, subclinical ischemia, or a combination thereof. Both scenarios are typically associated with significant morbidity and mortality.

A goal of HD usually is to bring ESRD patients to their dry weight, or the weight at which their extracellular volume is optimized. Determining a patient's true dry weight can be challenging. There are no accurate, fast, and/or nan-invasive objective methods to monitor fluid status to determine whether a patient's extracellular volume is physiologic. The standard technique relies on a combination of subjective measurements, such as estimating the degree of lower-extremity edema through palpation, and/or measurements subject to confounding, such as weight change (Ishibe, S. et al. *Semin. Dial.* 17, 37-43 (2004); Agarwal, R. et al. *Clin. J. Am. Soc. Nephrol.* 5, 1255-60 (2010); Fallick, C. et al. *Circ. Heart Fail.* 4, 669-75 (2011); and Agarwal, R. *Am. J. Nephrol.* 38, 75-77 (2013)).

A quantitative sensor to detect volume overload may have to potential to benefit patient populations beyond simply those with ESRD. It is estimated that more than 6 million patients in the US suffer from acute (e.g., sepsis, post-surgical) or chronic (e.g., congestive heart failure) fluid overload (Jessup, M. et al. *N. Engl. J. Med* 348, 2007-18 (2003); Frank, W. et al. *Congest. Hear. Fail*. Supplement, S45-51 (2010); Walsh, S. R. et al. Int. J. Clin. Pract. 62, 492-497 (2008)). Managing hypervolemia and its complications costs the US healthcare system over $35 billion annually (see, e.g., Ekinci, C. et al. *Blood Purif* 46, 34-47 (2018)).

Bioimpedance (BI) is a non-invasive technology frequently used for fluid assessment. BI utilizes skin-surface electrodes to deliver a multi-frequency, low-level current into the body. The more fluid that is present, the less resistance the current encounters when traversing the body. The challenge for BI is that many factors, such as body geometry and skin properties, also affect resistance (see, e.g., Ishibe, S. et al. *Semin. Dial.* 17, 37-43 (2004)).

BI accounts for these multiple factors by developing population-specific equations to correlate the measured resistance (and reactance) to fluid volumes. One of the limitations of BI is that it typically does not work well when applied to patients outside of the population on which the predictive algorithms were developed (Dehghan, M. et al. *Nutr. J.* 7, 26 (2008)).

Nuclear magnetic resonance (NMR) relaxometry can provide a direct, non-invasive measurement of fluid volume and its environment (Mathur-De Vré. R., *Prog. Biophys. Mol. Biol.* 35, 103-34 (1979)). MRI is more reliable than bio-impedance when measuring muscle hydration but if is, however, usually impractical for routine use, typically due to its limited availability and/or restriction to the scanner suite. Portable NMR sensors can perform the same quantitative measurements as MRI scanners, while also being convenient for routine use. A variety of portable NMR sensor designs exist, many of which are single-sided (also known as unilateral, strayfield, or inside-out NMR). These devices can permit the magnet to be placed on the surface of the sample instead of surrounding it. Single-sided designs can allow the sensor to be smaller than it would otherwise have to be to accommodate large samples. Portable NMR sensors are also often non-imaging, as they are designed to take quantitative NMR relaxometry measurements of a bulk sample, rather than thin, slice-wise measurements. Non-imaging NMR sensors have long been used in oil well logging (see, e.g., Coates, G. R. et al. *NMR Logging: Principles and Applications* (Houston. 1999)), food quality control (Todt, H. et al. *Food Chem.* 96, 436-440 (2006), and airport security (Apih. T. et al. NATO *Advanced Research Workshop on Magnetic Resonance Detection of Explosives and Illicit Materials*, (Springer, Izmir, Turkey, 2012)). Single-sided sensors have more recently been used in quantifying properties of biological tissues, such as skin, tendon, and breast tissue (see, e.g., Tourell, M. C. et al. *Magn. Reson. Med.* 80, 1243-1251 (2018)).

The amount of baseline hypervolemia typically encountered in maintenance HD patients represents the level of fluid overload for which it would be advantageous to have accurate clinical sensors. Clinicians would benefit from a sensor that can detect the type of lower-level hypervolemia (<5 L) in patients receiving chronic hemodialysis. Physical signs are typically not visible at this level of hypervolemia, yet are associated with increased morbidity and mortality (see, e.g., Ekinci, C. et al. *Blood Purif.* 46, 34-47 (2018).

There remains a need for better methods and devices for monitoring the volume status of patients, including devices and methods that are more easily accessible (e.g., may be performed bedside), and/or devices and methods that can detect a patient's fluid level before physical signs of an improper fluid level are detectable.

BRIEF SUMMARY

Provided herein are improved methods of fluid assessment, including methods that can detect an expanded muscle extracellular space, which is a first sign of fluid overload that, at an early stage, is undetectable by physical exam.

In one aspect, methods of determining a fluid status of a patient are provided. In some embodiments, the methods for determining a fluid status of a patient include measuring a quantitative relaxation time (T2) of a muscle of the patient; and determining whether the patient is hypovolemic, euvolemic, or hypervolemic. The muscle may be a muscle of an extremity. In some embodiments, the muscle of the patient is a leg muscle, such as a calf muscle.

In another aspect, methods of treatment are provided. In some embodiments, the methods of treatment include determining a first fluid status of a patient by measuring a first quantitative relaxation time (T2) of a muscle of the patient; and administering to the patient a first treatment comprising a fluid reduction treatment or a hydration treatment if the first fluid status of the patient is hypervolemic or hypovolemic, respectively. The methods of treatment may also include determining a second fluid status of the patient after the administering of the first treatment by measuring a second quantitative relaxation time (T2) of a muscle of the patient; and administering to the patient a second treatment comprising a fluid reduction treatment or a hydration treatment if the second fluid status of the patient is hypervolemic or hypovolemic, respectively. The fluid reduction treatment may include hemodialysis.

Additional aspects will be set forth in part in the description which follows, and in part will be obvious from the description, or may be learned by practice of the aspects described herein. The advantages described herein will be realized and attained by means of the elements and combinations particularly pointed out in the appended claims. It is to be understood that both the foregoing general description and the following, detailed description are exemplary and explanatory only and are not restrictive.

DETAILED DESCRIPTION

Figure 1:
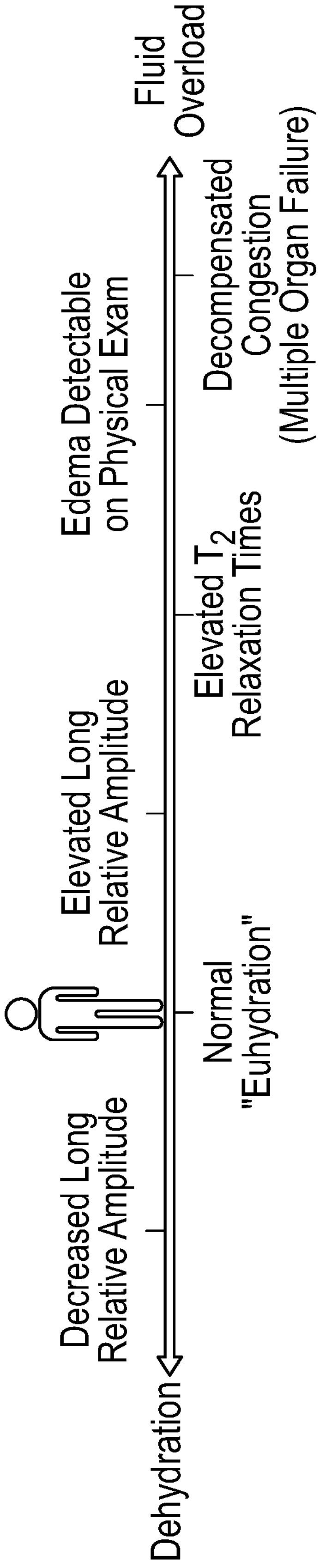
FIG. 1 depicts a summary of patient status and the corresponding relaxometry results of embodiments of the methods described herein.

Provided herein are methods that, in some embodiments, permit the extent and/or location of a patient's fluid change (e.g., a fluid decrease) to be quantified. The quantification may be achieved with MRI or an NMR sensor, such as a portable NMR sensor, including when ECF volume scales with $RA_{long}$ or $RA_b$, respectively, as described herein.

Methods for Determining Fluid States

Methods are provided herein for determining a fluid status of a patient. In some embodiments, the methods include measuring a quantitative relaxation time (T2) of a muscle of the patient, and determining whether the patient is hypovolemic, euvolemic, or hypervolemic.

A patient is "euvolemic" when the patient's fluid volume is within a normal range. The patient's fluid volume includes the patient's blood volume, interstitial fluid volume, and intracellular fluid volume. A patient is "hypovolemic" when the patient's fluid volume is less than the smallest fluid volume within the normal range. A patient is "hypovolemic" when the patient's fluid volume is greater than the largest fluid volume within the normal range.

A quantitative relaxation time may be measured at any time. In some embodiments, the measuring of the quantitative relaxation time (T2) is performed before, during, and/or after, the patient is treated with dialysis or other treatments, including a treatment that may alter a patient's fluid volume.

Examples of relaxation parameters and methods for measuring relaxation parameters, which may be used in any of the methods herein, are described at U.S. Patent Application Publication No. 2016/0120438, which is incorporated herein by reference. The relaxometry measurements of the methods described herein may be interpreted in view of one or more physiologic mechanisms in place to regulate the distribution of salt and water. In the absence of kidney function (e.g., end-stage renal disease), substantially all salt and water intake is retained (except for small amounts that can be lost via gastrointestinal and insensible excretion), which can lead to expansion of the vascular space. Typically, a muscle's rich microvasculature network can cause an initial predominance of interstitial fluid accumulation in the muscle, as opposed to less vascular tissues. Eventually, the capacity of a muscle to hold excess water can be exceeded, and lymphatic drainage is necessary. Lymphatic reabsorption typically occurs primarily in the subcutaneous tissue space, which is likely why perifascial fluid and subcutaneous edema are observed in more advanced cases of fluid overload. It is believed that the removal of fluid via the vascular space, as in HD, leads to fluid removal in the same order as accumulation occurred, with well-vascularized muscle responding first.

In some embodiments, the measuring of the quantitative relaxation time (T2) comprises determining a relative amplitude of a long component of the muscle (e.g., $RA_b$ or $RA_{long}$, as described herein), the long component having a longer relaxation time than a short component of the muscle. As described herein, a short component (relaxation time and amplitude) of a muscle may relate to intracellular fluid (ICF), whereas a long component may relate to extracellular fluid (ECF).

Typically, a sample that is in a more liquid state (e.g., free fluids, ascites, edema, etc.) has a longer relaxation time, whereas a sample that has restricted mobility (e.g., cellular water bound to macromolecules) has a shorter relaxation time. Amplitude is a measure of the number of protons in a particular molecular environment; therefore, relative amplitude can measure the quantity of atoms in a particular environment compared to the quantity of atoms in all other environments.

In some embodiments, the methods provided herein include determining, based on a relative amplitude of a long component, a ratio of extracellular fluid to intracellular fluid of the muscle.

An increase or decrease in the relative amplitude of the long component compared to a reference relative amplitude may indicate an increase or decrease, respectively, of (i) a volume of the muscle's extracellular fluid space, or (ii) an amount of extracellular fluid in the muscle, which indicate an increase or decrease, respectively, in a hydration level of the patient. In some embodiments, an increase or decrease in the relative amplitude of the long component compared to a reference relative amplitude indicates an increase or decrease, respectively, of a volume of a muscle's extracellular fluid space, which indicates an increase or decrease, respectively, in a hydration level of the patient, in some embodiments, an increase or decrease in the relative amplitude of the long component compared to a reference relative amplitude indicates an increase or decrease, respectively, of an amount of extracellular fluid in a muscle, which indicates an increase or decrease, respectively, in a hydration level of the patient.

A reference relative amplitude may be (i) calculated based on one or more characteristics of the patient, (ii) determined when the patient is euvolemic, or (iii) collected from a control patient. The one or more characteristics of the patient may include the patient's height, baseline body weight, amount of fluid removed from the patient during treatment, or a combination thereof.

Methods of Treatment

Methods of treatment also are provided herein. In some embodiments, the methods of treatment include determining a first fluid status of a patient by measuring a first quantitative relaxation time (T2) of a muscle of the patient, as described herein, and then administering to the patient a treatment comprising a fluid reduction treatment or a hydration treatment if the first fluid status of the patient is hypervolemic or hypovolemic, respectively.

The methods of treatment also may include determining a second fluid status of the patient after the first treatment by measuring a second quantitative relaxation time (T2) of a muscle of the patient, and administering to the patient a second treatment comprising a fluid reduction treatment or a hydration treatment if the second fluid status of the patient is hypervolemic or hypovolemic, respectively. The fluid status of the patient may be determined any number of times. For example, the methods of treatment may include determining a third fluid status of the patient after the second treatment by measuring a third quantitative relaxation time (T2) of a muscle of the patient, and administering to the patient a third treatment comprising a fluid reduction treatment or a hydration treatment if the third fluid status of the patient is hypervolemic or hypovolemic, respectively.

A patient determined to be hypovolennt: may be treated to control the route by which fluids are lost, for example, by administering medication or changing an environment to reduce diarrhea, vomiting, transcutaneous losses, etc. Alternatively, or in combination with the aforementioned therapy, the patient may be treated by oral rehydration therapy or fluid replacement, for example, by intravenous or subcutaneous therapy. Oral rehydration therapy may include administering an aqueous solution orally (e.g., water or water-containing electrolytes). Fluid replacement therapy may include administering an aqueous solution intravenously or subcutaneously (e.g., saline).

A patient determined to be hypervolemic may receive a fluid reduction treatment that includes hemodialysis. A patient determined to be hypervolemic may be treated by administering a diuretic (e.g., thiazide or mannitol), a beta-blocker, an angiotensin-converting enzyme (ACE) inhibitor (e.g., captopril), a vasopressin receptor antagonist (e.g., conivaptan, lixivaptan, or satavaptan), or a combination thereof. Another treatment of hypervolemia (e.g., congestion) may be ultrafiltration, which includes the mechanical removal of fluid from the blood stream.

Administration of an appropriate therapy to a patient may be triggered automatically by placing a device for measuring a relaxation time in communication with a computer, which is in communication with an apparatus that is capable of implementing (e.g., dispensing) any of the above-described therapies or any other appropriate therapy. Alternatively, administration of an appropriate therapy may include self-administration or administration by medical personnel.

A patient undergoing treatment for hydration imbalance may be monitored using the methods described herein to prevent overdosing the treatment. The rate of measurements included in the methods of the invention allows quick monitoring of the subject and provides sufficient time for a response (e.g., adjustment of the treatment) to the changes in the hydration state of the patient.

Relaxometry Devices

The devices used in the methods described herein may include any devices capable of measuring a quantitative relaxation time (T2). In some embodiments, the device is configured to measure the quantitative relaxation time (T2) with a single measurement.

The devices may be configured to measure any volume of muscle tissue that is sufficient to achieve an effective measurement of a quantitative relaxation time (T2). In some embodiments, the device is configured to measure a voxel comprising about 0.1 $cm^3$ to about 1 $cm^3$ of the muscle of a patient, about 0.2 $cm^3$ to about 0.9 $cm^3$, about 0.3 $cm^3$ to about 0.8 $cm^3$, about 0.4 $cm^3$ to about 0.7 $cm^3$, about 0.4 $cm^3$ to about 0.6 $cm^3$, or about 0.5 $cm^3$ of muscle.

In some embodiment, the device is an NMR sensor. The NMR sensor may be a portable NMR sensor. A "portable NMR sensor" is an NMR sensor having dimensions that permit the sensor to be (i) transported (e.g., between rooms at a clinic or hospital) with relative ease, (ii) used at a patient's bedside, or (iii) a combination thereof. In some embodiments, a portable NMR sensor may have dimensions that do not exceed 30 cm×30 cm×30 cm. The NM R sensor, such as a portable NMR sensor, may be a single-side NMR sensor, or a single-voxel, single-side NMR sensor, such as a 0.28 T single-voxel single-side NMR sensor.

In some embodiments, a portable, non-imaging, single-sided NMR sensor is used to assess rapidly clinically-relevant changes in the ECF of hypervolemic ESRD patients, and optionally differentiate them from euvolemic healthy controls with stable volume status. The NMR sensors used in the methods described herein are not limited to single-sided designs, permanent magnets, or a combination thereof. The NMR sensors may rely on lower field strengths, different purpose-built magnet constructions (e.g., optimized for curved surfaces or greater penetration depths), and other parts of the anatomy (e.g., lung, abdomen, etc.). The measurement of additional relaxometry parameters, like T1, or taking two-dimensional measurements like T2-Diffusion or T1-T2 also may be used, and these parameters may permit further probing into the physiology.

In some embodiments, the device is a MRI device. The MRI device may include a wherein the magnetic resonance imaging device is a 1.5 T MRI device. The MRI device may share one or more features with the NMR devices described herein.

Muscles

Any muscle of a patient may have a quantitative relaxation time (T2) measured according to the methods described herein.

In some embodiments, the muscle of the patient is a muscle of an extremity. In some embodiments, the muscle of the patient is a leg muscle.

In some embodiments, the muscle of the patient is a calf muscle. In some embodiments, the muscle of the patient is a muscle of a finger, a toe, a foot, a calf, a hand, a wrist, a leg, or an arm.

Patient Characteristics

Any patient may be subjected to the methods described herein, including patients having one or more diseases or conditions. In some embodiments, the patient has end-stage renal disease.

In some embodiments, the patient has a disease or condition selected from the group consisting of congestive heart failure (CHF), renal failure, liver cirrhosis, nephrotic syndrome, brain swelling, diabetes, staphylococcal infection, nephrolithiasis, diarrhea, colitis, preferably ulcerative colitis, pyelonephritis, cystic fibrosis, Huntington's disease, rotavirus infection, herpangina, salmonellosis, norovirus infection, pertussis, cryptosporidium infection, cholera, coma, and water intoxication.

In addition to sensing fluid status, the methods described herein for conducting point-of-care relaxometry can have other uses, such as monitoring the progression of multiple sclerosis, assessing iron overload in the liver, and identifying inflammatory muscular disorders. Portable NMR sensors can make it economically feasible to bring these new diagnostic discoveries to the clinic and improve patient care.

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

The present disclosure may address one or more of the problems and deficiencies of known methods and processes. However, it is contemplated that various embodiments may prove useful in addressing other problems and deficiencies in a number of technical areas. Therefore, the present disclosure should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

In the descriptions provided herein, the terms “includes,” “is,” “containing,” “having,” and “comprises” are used in an open-ended fashion, and thus should be interpreted to mean “including, but not limited to.” When methods or systems are claimed or described in terms of “comprising” various steps or components, the methods or systems can also “consist essentially of” or “consist of” the various steps or components, unless stated otherwise.

The terms “a,” “an,” and “the” are intended to include plural alternatives, e.g., at least one. For instance, the disclosure of “a relaxation time,” “a muscle,” “an NMR device”, and the like, is meant to encompass one, or mixtures or combinations of more than one relaxation time, muscle, NMR device, and the like, unless otherwise specified.

Various numerical ranges may be disclosed herein. When Applicant discloses or claims a range of any type, Applicant’s intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in some embodiments, that a portable nuclear magnetic resonance sensor is configured to measure a voxel about 0.2 $cm^3$ to about 1 $cm^3$ of the muscle of the patient. This range should be interpreted as encompassing about 0.2 $cm^3$ to about 1 $cm^3$, and further encompasses “about” each of 0.3 $cm^3$, 0.4 $cm^3$, 0.5 $cm^3$, 0.6 $cm^3$, 0.7 $cm^3$, 0.8 $cm^3$, and 0.9 $cm^3$, including any ranges and sub-ranges between any of these values.

As used herein, the term “about” means plus or minus 10% of the numerical value of the number with which it is being used.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Analysis of Subjects at Different Fluid States

The experiments described in the following examples demonstrate that a portable nuclear magnetic resonance (NMR) sensor was able to assess individual fluid status changes at the bedside at a fraction of the time and cost of MRI.

For these experiments, end-stage renal disease (ESRD) patients were recruited who regularly received dialysis treatments with intradialytic fluid removal as a model of volume overload, as well as healthy control patients as a model of euvolemia.

Quantitative T2 measurements of the lower leg of ESRD patients immediately before and after dialysis were compared to those of euvolemic healthy controls using both a 0.28 T bedside single-voxel sensor and a 1.5 T clinical scanner.

It was discovered that the first sign of fluid overload was an expanded muscle extracellular fluid (ECF) space, which was a finding undetectable at this stage on physical exam. A decrease in muscle ECF upon fluid removal was similarly detectable with the bedside sensor. Bioimpedance results generally performed worse than MRI and comparably to the bedside NMR sensor. These findings suggested that bedside NMR measurements may be an important method to identify fluid overload early in ESRD patients, and potentially other patient populations as well.

Seven patients with ESRD maintained with chronic thrice weekly hemodialysis (HD), and seven healthy controls (HC) were recruited. One HC subject and two HD subjects completed the study twice. Enrollment was limited to males over the age of 25 years, with a body mass index (BMI) between 18.5-40. Patients were excluded if they had a pacemaker, metal implants, severe anemia (Hgb<7.5 mg/dL), or had a history of limb amputation. HC subjects reported no history of renal disease, cardiac disease, or other chronic conditions. HD and HC subjects were age-matched by decade. Basic demographics were recorded for all participants.

All enrolled HD patients were fluid overloaded, which was apparent from their clinical records of weight gain above their dry weight and the successful removal of fluid during their observed HD treatment. As is routine for dialysis treatments, ultra-filtration volume was informed by the change in weight from their target dry weight.

Measurements were taken of HD subjects before and after a single HD session, which allowed for a paired-assessment of each subject at both a baseline state of hypervolemia and a later state closer to euvolemia following fluid removal. HCs sat in the same hospital bed as HDs for 4 hours, which is the length of a typical dialysis session. It was assumed that NC subjects maintained a stable volume status throughout the study.

T2 relaxation measurements were taken at the upper calf in all subjects with both a 1.5 T MRI and a 0.28 T single-voxel, single-sided NMR sensor at the beginning and end of the study visit. Bioimpedance measurements, weight, vital signs, and blood draws were also taken at the same two time points. The demographics of the study cohort of this example are summarized at Table 1.

TABLE 1

Demographics Summary of Study Cohort

| | | Reference Range | Healthy Controls (HC) | Hemodialysis Subjects (HD) |
|---|---|---|---|---|
| n | # | | 7 (6 unique) | 7 (5 unique) |
| Age | yrs | | 54.2 ± 4.9 | 55.1 ± 10.3 |
| % White | | | 85.7% | 42.9% |
| BMI | $kg/m^2$ | 18.5-24.9 | 25.1 ± 4.4 | 27.8 ± 5.0 |

TABLE 1-continued

| Demographics Summary of Study Cohort | | | | |
|---|---|---|---|---|
| | | Reference Range | Healthy Controls (HC) | Hemodialysis Subjects (HD) |
| Baseline Weight | kg | | 75.4 ± 12.2 | 82.8 ± 16.1 |
| Fluid Loss | kg | | 0.6 ± 0.2 | 2.2 ± 1.2 |
| Fluid Loss | % | | 1.2 ± 0.5 | 4.3 ± 2.5 |
| HD vintage | days | | NA | 1013 ± 699.8 |
| Sodium | mmol/L | 134-144 | 140.6 ± 2.1 | 139.1 ± 1.6 |
| BUN | mg/dL | 6-24 | 16.0 ± 4.4 | 58.1 ± 14.5 |
| Creatinine | mg/dL | 0.76-1.27 | 0.8 ± 0.2 | 8.3 ± 1.8 |
| WBC | ×10e3/uL | 3.4-10.8 | 5.0 ± 1.6 | 7.6 ± 1.1 |
| Platelets | ×10e3/uL | 150-379 | 255.3 ± 77.1 | 184.3 ± 87.4 |
| Osmolality | mOsm/kg | 275-295 | 291.6 ± 5.8 | 307.7 ± 4.1 |
| proBNP | pg/mL | <300 | 18.4 ± 5.4 | 6086.1 ± 4495.9 |

The reported blood value results of Table 1 were from baseline blood draws. Fluid loss (in kg) was based on the change in pre- and post-weight. The percentage fluid loss was calculated by 100%*Fluid Loss/(0.6*Baseline Weight), because approximately 60% of the body is water. The values represent Mean±Standard Deviation.

Quantitative relaxometry—through both traditional MRI and non-imaging NMR sensors—was used provide data about a patient's fluid status. Recruiting dialysis patients allowed the study of a hypervolemic population that became less hypervolemic at the end of the study, thereby allowing; for paired analyses of the same person at two distinct fluid levels.

Healthy controls were assumed to remain euvolemic throughout the study, though a few unexpected cases of dehydration were encountered. Even with the relatively small sample size of the tests of the examples herein, the results permitted a differentiation between subjects who were euvolemic or had varying degrees of volume overload (FIG. 1). In addition, the MRI results seemed sensitive to subjects that showed evidence of dehydration.

FIG. 1 depicts a schematic summary of the relaxometry findings of the examples herein—through both traditional MRI and portable NMR sensor—at different clinical fluid states. The findings of FIG. 1 were observed in the muscular tissue.

None of the subjects displayed clinical signs of volume overload on physical exam. The results of this example demonstrated that the relaxometry metrics described herein could detect fluid overload before traditional clinical examination, which is the principle test currently used by physicians.

Example 2—Tissue Changes in Response to Dialysis by MRI

As explained herein, the first sign of fluid overload in the calf region amongst the patients studied was an elevation in the $RA_{long}$ in the muscle, which indicated an expanded ratio of ECF to the ICF.

HD subjects were distinguished from euvolemic HC subjects with a single MRI measurement of $RA_{long}$ at a single time point. The two populations also could be distinguished via the MRI or NMR sensor's measurement of change in $RA_{long}$ and $RA_b$, respectively, which are related to a decrease in the relative ratio of muscle ECF.

The observed changes in $RA_{long}$ and $RA_b$ values were within the expected range, based on the percentage of fluid loss from study subjects. A study of the minimum necessary voxel size revealed that a NMR sensor that measures 0.5 $cm^3$ of the lateral or anterior muscles can distinguish HC versus HD subjects based on a single measurement as well.

The $T_{2,long}$ of the calf muscle amongst the most volume-overloaded patients was elevated, indicating that the molecular environment of the ECF space of these subjects became more aqueous than normal. Previously published studies of patients who were more volume-overloaded than the patient population of the current examples reported relaxation time increases in the calf muscle as well (see, e.g., Wang, J. Z. et al. Angiology, 358-365 (1991); and Meler, J. D. et al. J. Comput. Assist. Tomogr. 21, 969-73 (1997)). It is believed, however, that no studies have reported the $RA_{long}$ increase that precedes relaxation time elevation.

In this example, quantitative T2 MRI scans acquired at 1.5 were used to determine which tissues and parameters (if any) changed in response to HD. Regions of interest (ROIs) were drawn in the MRI images to select distinct tissue types and sub-muscle groups. ROIs were drawn on each slice of each scan for all subjects. The tissue types and sub-muscle groups included (i) subcutaneous tissue, which included skin, fat and blood vessels in the fat, (ii) bone and marrow, which included tibia and fibula, (iii) muscular tissue, which included muscle, fascia, nerves, and blood vessels, and (iv) whole leg, which included all tissues.

The T2 magnetization versus time (M(t)) data of each pixel was fit to an exponential decay model determined by the extra sum-of-squares F-test.

The optimal model was a bi-exponential decay for all tissues, except for bone, whose optimal model was mono-exponential. The mono-exponential model was a two-parameter fit which produced an amplitude and relaxation time ($A_{1,exp}$, $T_{2,1exp}$). The bi-exponential model was a four-parameter fit which produced amplitudes and relaxation times for the short and long time components ($A_S$, $T_{2,short}$, $A_L$, $T_{2,long}$). The short component (relaxation time and amplitude) of the bi-exponential fit of the muscle related to intracellular fluid (ICF), whereas the long component related to extracellular fluid (ECF) (see, e.g., Gambarota, G. et al. *Magn. Reson. Med,* 592-599 (2001); Ababneh, Z. et al. *Magn. Reson. Med.* 54, 524-31 (2005); Araujo, E. C. A. et al. *Biophys. J.* 106, 2267-2274 (2014); and Fan, R. H, et al. *NMR Biomed.* 21, 566-573 (2008)).

$$M(t)_{1exp} = A_{1exp}e^{-\frac{t}{T_{2,1exp}}}$$

$$M(t)_{2exp} = A_{short}e^{-\frac{t}{T_{2,short}}} + A_{long}e^{-\frac{t}{T_{2,long}}}$$

Transverse proton NMR relaxation time (T2) is a measure of molecular environment. A sample that is in a more liquid state (e.g., free fluids, ascites, edema) has a longer relaxation time. A sample that has restricted mobility (e.g., cellular water bound to macromolecules) has a short relaxation time. Amplitude is a measure of the number of protons in a particular molecular environment. Relative amplitude measures the quantity of atoms in a particular environment compared to the quantity of atoms in all other environments. The relative amplitude of the long component, $RA_{long}$ (i.e., related to the relative amount of ECF in muscle), for example, was calculated by:

$$RA_{long} = \frac{A_{long}}{A_{short} + A_{long}} \times 100\%$$

Figure 2A:
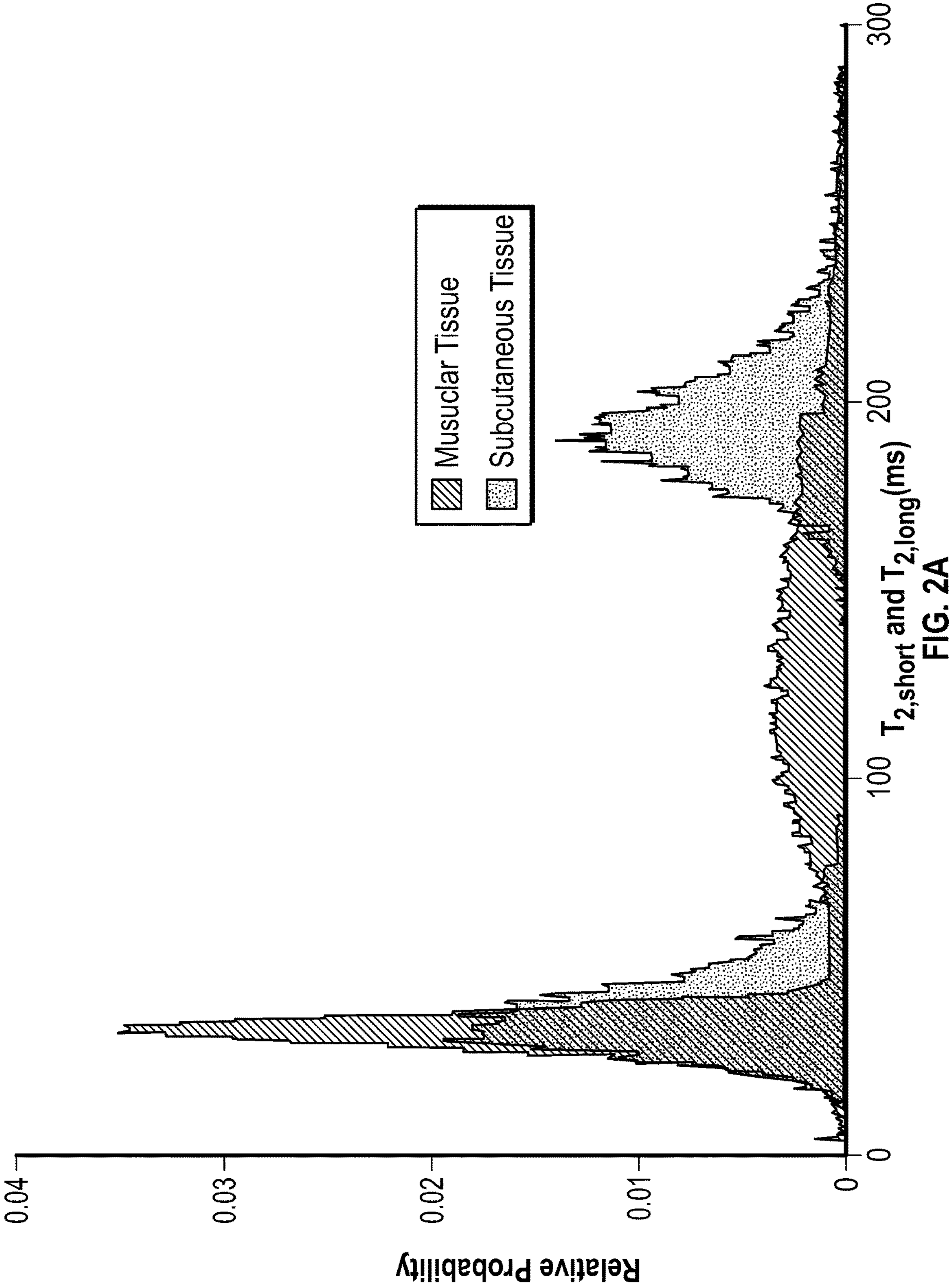
FIG. 2A depicts a histogram of the pixel-wise short ($T_{2,short}$) and long ($T_{2,long}$) relaxation values found in the muscular and subcutaneous tissue of a representative patient when subjected to an embodiment of the methods described herein.

FIG. 2A depicts the pixel-wise $T_{2,short}$ and $T_{2,long}$ for muscle and subcutaneous tissue. The $T_{2,short}$ values were similar while the $T_{2,long}$ values differed significantly with the subcutaneous compartment having the longer $T_{2,long}$.

Figure 2B:
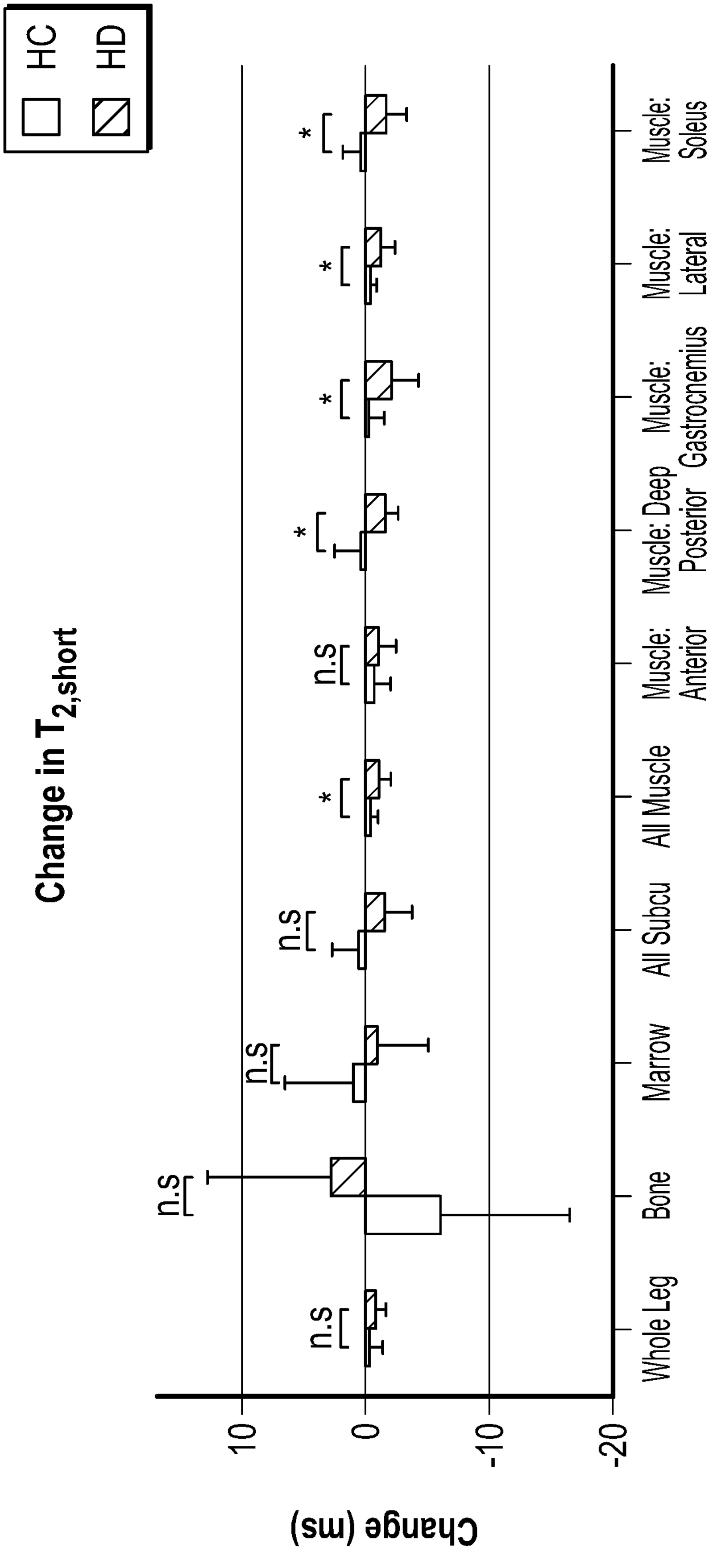
FIG. 2B depicts the pre-post change in $T_{2,short}$ for various regions of interest for patients subjected to an embodiment of the methods described herein.
Figure 2C:
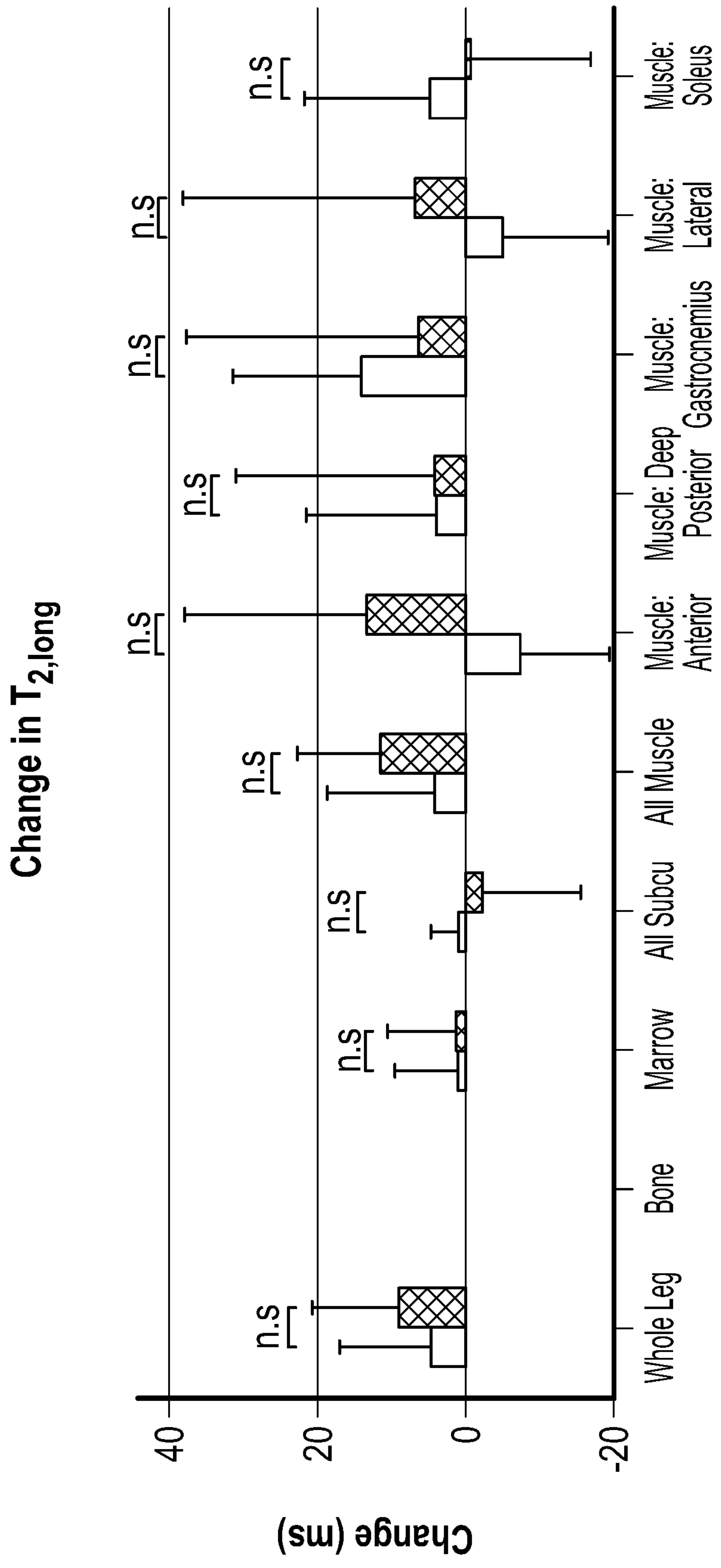
FIG. 2C depicts the pre-post change in $T_{2,long}$ for various regions of interest for patients subjected to an embodiment of the methods described herein.
Figure 2D:
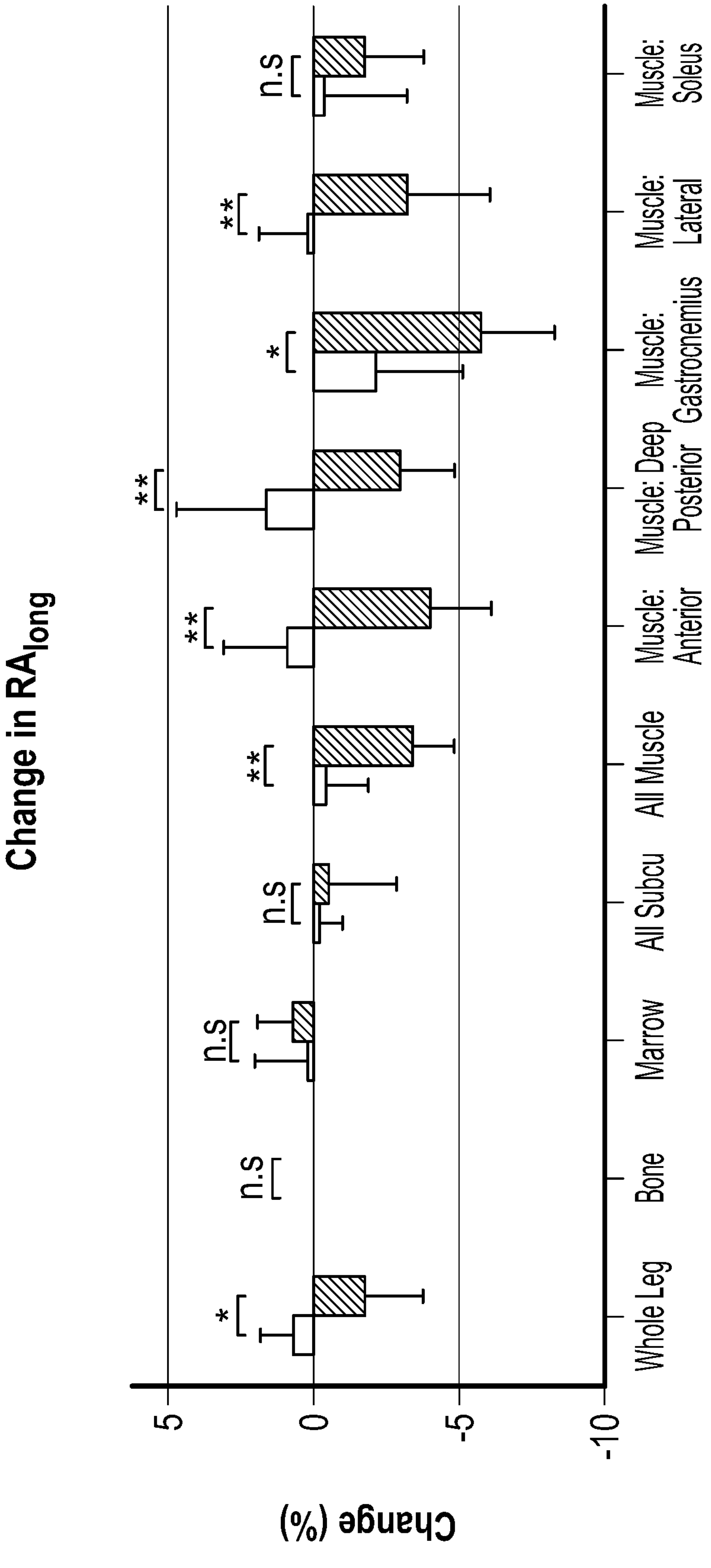
FIG. 2D depicts the pre-post change in $RA_{long}$ for various regions of interest for patients subjected to an embodiment of the methods described herein.

The change from pre- to post-measurement was calculated for each parameter ($T_{2,short}$, $T_{2,long}$, $RA_{long}$) in each tissue type. FIG. 2B, FIG. 2C, and FIG. 2D depict the pre-post change $T_{2,short}$ (FIG. 2B), $T_{2,long}$ (FIG. 2C), and $RA_{long}$ (FIG. 2D) for each ROI across all HC and HD subjects. Bars represent the mean±SD. ns denotes $p \geq 0.05$, *for $p<0.05$, **for $p<0.01$.

The muscle, muscle sub-groups, and whole leg (which includes primarily muscle) were the only tissues in this example to display statistically significant changes in response to dialysis of which the change was primarily in $RA_{long}$.

In this example, $RA_{long}$ changed by about 1% to about 7% across various tissues in the leg. It was possible to calculate the expected change in total body water based on the amount of fluid removed from each subject, their baseline body weight, and the fact that the body is composed of about 60% water (see, e.g., Taal, M. W. et al. *Brenner and Rector's The Kidney*, Elsevier Health Sciences, 2011).

$$\text{Expected \% Change in Body Water} = \frac{\text{Change in Fluid (kg)}}{0.6 * \text{Baseline Body Weight (kg)}} \times 100\%$$

Observing body water changes of about 1.2±0.5% (min: 0.8%, max: 2.2%) was expected in HCs and 4.3±2.6% (min: 1.1%, max: 8.9%) body water changes in HDs (see Table 1), which was consistent with the reported $RA_{long}$ values at FIG. 2D. it was not expected for the $RA_{long}$ values to match perfectly because changes in ECF may not directly track TBW changes, and certainly not in specific tissues.

Example 3—MRI—T2 Relaxation Times

The change in pixel-wise T2 relaxation times was compared between HCs and HDs across each ROI (FIG. 2B and FIG. 2C).

While the change in the short relaxation time achieved statistical significance in some muscle subgroups, the size of these changes was small (e.g., <5 ms), which did not make it an ideal indicator in the foregoing examples, and was of little diagnostic consequence since relaxation time measurements typically have a precision of a few milliseconds. In this example, long relaxation times, $T_{2,long}$, did not have any statistically significant changes anywhere in the leg when average HC and HD values were compared.

There were three subjects, however, that, upon individual inspection, had quantifiably elevated $T_{2,long}$ values: HD1, HD1b, HD2b. A cumulative probability (cdf) plot of $T_{2,long}$ in the whole leg revealed that these three subjects had relaxation times that were greater than the 95% confidence interval of all subjects (FIG. 3A).

Figure 3A:
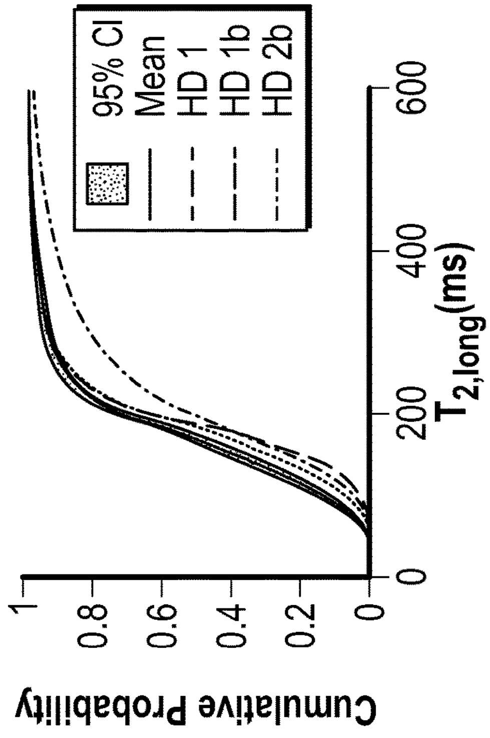
FIG. 3A depicts cumulative probability plots of $T_{2,long}$ in the whole leg of various patients subjected to an embodiment of the methods described herein.

FIG. 3A depicts cdf plots of the pixel-wise $T_{2,long}$ values found within the entire leg at baseline. The mean and 95% confidence interval (CI) of all subjects is provided.

HD includes both ultrafiltration and removal of waste. It was expected that filtration might affect the relaxation times, rather than the relative amplitudes, since relaxation time is a measure of molecular environment. Furthermore, urea—a compound that accumulates in the body of ESRD patients—is a known T2-shortening agent that diffuses through all fluid spaces in the body (see, e.g., Bhave, G. et al. *Am. J. Kidney Dis.* 58, 302-309 (2011)).

If levels of urea were affecting the relaxometry measurements, it would have been expected for the T2 relaxation times to be lower in HD subjects than in HCs, and then to increase after dialysis. In this example, however, T2 relaxation times of HD subjects were equal to or greater than those of HCs at all time points (FIG. 3A).

HD1, HD1b, and HD2b had among the highest serum brain natriuretic peptide (BNP) levels, one blood biomarker for volume overload (see Table 2). The reference range for proBNP was <300 pg/mL.

TABLE 2

Summary of the proBNP and Clinical Examination Results for HD Subjects.

| Subject | Elevated T2 | Pitting Edema | proBNP (pg/mL) |
|---|---|---|---|
| HD 2b | Yes | No | 15000 |
| HD 1b | Yes | No | 8815 |
| HD 3 | No | No | 7500 |
| HD 1 | Yes | No | 4100 |
| HD 2 | No | No | 3400 |
| HD 4b | No | No | 2900 |
| HD 5 | No | No | 608 |

HD2b and HD1 had perifascial fluid deposits and subcutaneous edema visible on the MRI scans (though not detected on physical exam), which are pre-cursors to pitting edema, and were visible in heatmaps as elevated relaxation time values bordering the leg. Heatmaps of $T_{2,short}$ and $T_{2,long}$ were collected for a sample healthy control, HD1, and HD2b. Perifascial fluid deposits and/or subcutaneous edema were observed, and the fluid deposits and edema were not detectable on clinical exam.

Example 4—RI—Relative Amplitudes

Figure 3B:
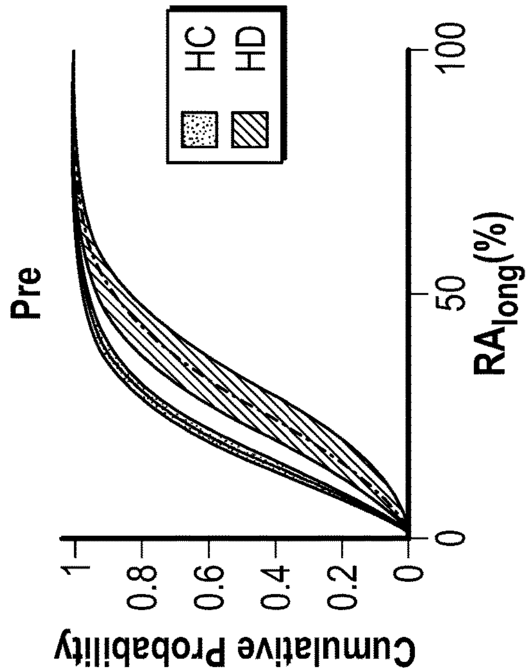
FIG. 3B depicts the average cumulative probability plots of the pixel-wise $RA_{long}$ in the muscle at pre-time points for various patients tested according to an embodiment of the methods described herein.
Figure 3C:
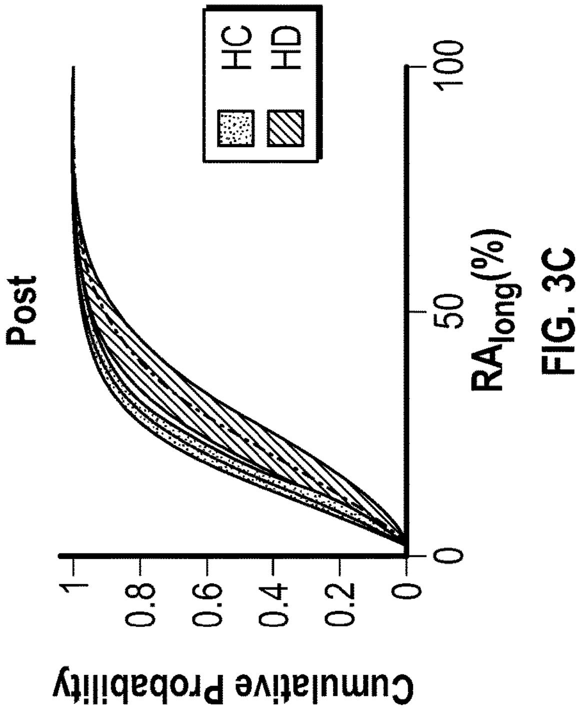
FIG. 3C depict the average cumulative probability plots the pixel-wise $RA_{long}$ in the muscle at post-time points for various patients tested according to an embodiment of the methods described herein.

The majority of HD subjects had elevated long relative amplitudes, $RA_{long}$, within the muscle compared to HCs at baseline. An elevated $RA_{long}$ value suggested that the ECF space of the tissue was expanded. The average $RA_{long}$ for HD subjects was significantly higher than that of HC's at every percentile at baseline, which was expected since HDs were hypervolemic and HCs were euvolemic at baseline (FIG. 3B). FIG. 3B and FIG. 3C depict the average cdf of the pixel-wise $RA_{long}$ in the muscle for HC and HD subjects pre- and post-time points, respectively.

Figure 3D:
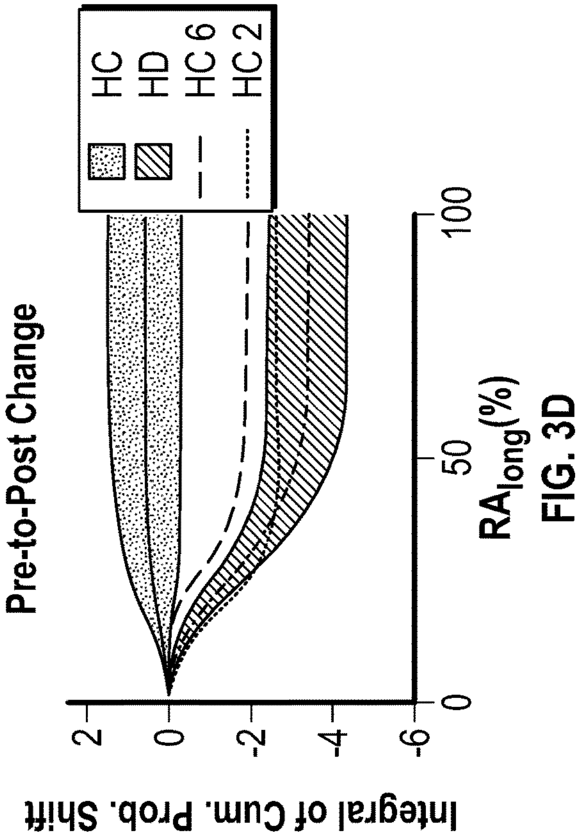
FIG. 3D depicts the change in $RA_{long}$ for two subject groups tested according to an embodiment of the methods described herein.

The relative size of the ECF space, $RA_{long}$, of the muscle decreased in response to HD such that relative ratios of ECF were more like those of euvolemic HCs (FIG. 3C, FIG. 3D). Reducing excess ECF so that the patient reaches a euvolemic state typically is one of the main objectives of hemodialysis. FIG. 3D depicts the change in $RA_{long}$ HC and HD subject groups. All cdf curves were plotted as mean±95% CI.

The fitting of relaxivity data also was performed on entire ROIs, which is a type of analysis similar to that of single-voxel NMR sensors, rather than on individual pixels. FIG. 4A show the results of this example before and after HD for the $RA_{long}$ of the muscle ROI. FIG. 4A depicts the $RA_{long}$ values of the muscle ROI for each subject. Three HD patients had post-dialysis $RA_{long}$ values that were within the $RA_{long}$ range of euvolemic healthy controls.

Figure 4B:
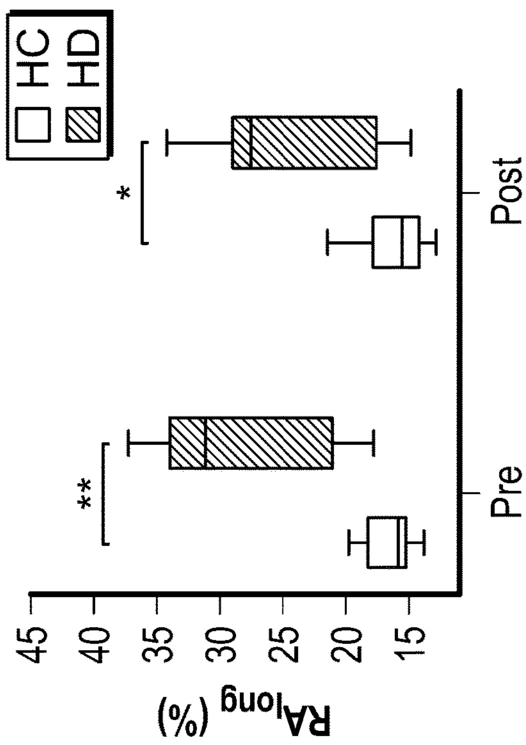
FIG. 4B depicts the data of FIG. 4A in a different format.

FIG. 4B shows the same data in boxplot form. The average muscle $RA_{long}$ for HD patients was 28.1%, while that of HCs was only 16.5%, with a statistical significance of p=0.0025 between the groups.

Figure 4C:
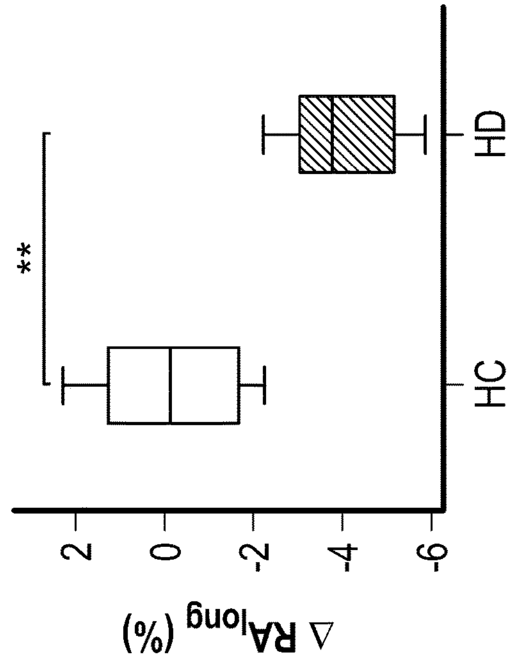
FIG. 4C depicts the change in $RA_{long}$ before and after dialysis for two subject groups tested according to an embodiment of this example.
Figure 4A:
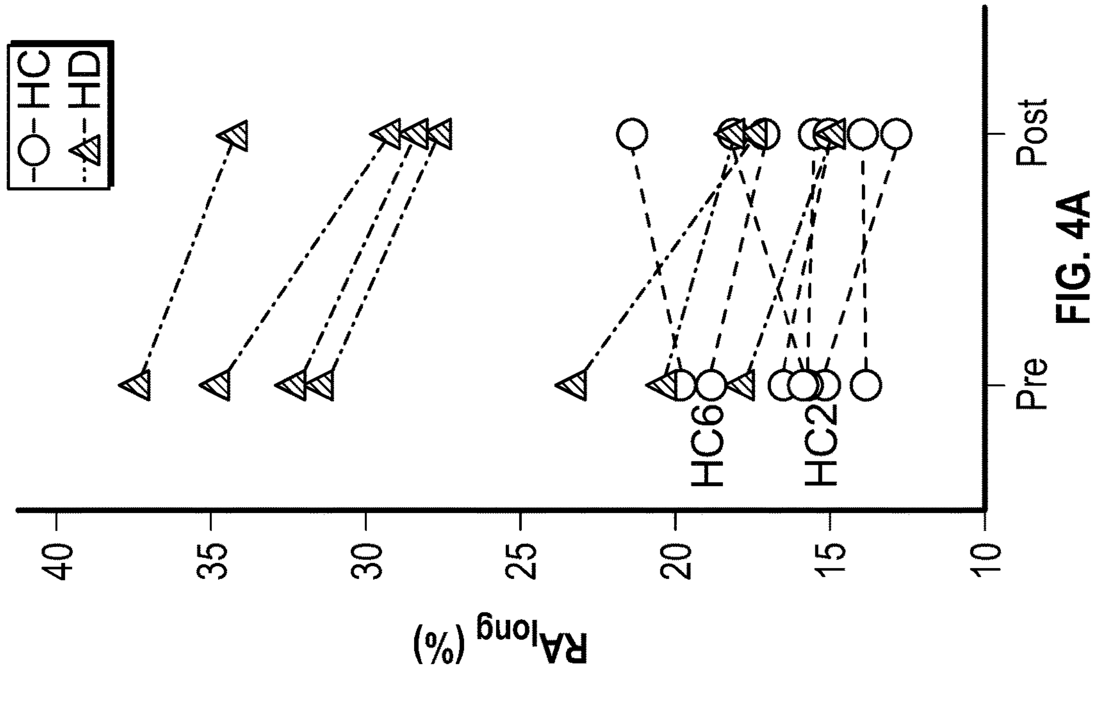
FIG. 4A depicts the $RA_{long}$ values of the muscle region of interest for patients tested according to an embodiment of the methods described herein.

FIG. 4C depicts the change in $RA_{long}$ before and after dialysis for the HD and HC groups of this example. No significant change in $RA_{long}$ occurred with HC subjects (p=0.7499) but HDs decreased by 4% (p=0.0157).

HC subjects did not, in fact, have significant changes in fluid status whereas HD patients had a recorded volume of fluid removed.

The observations of this example were statistically significant on the average and, additionally, a closer look revealed some interesting detail. There were two HC subjects—HC2 and HC6—that, like HDs, experienced a decrease in $RA_{long}$ the muscular tissue (FIG. 3D and FIG. 4A).

It was hypothesized that these two subjects became dehydrated over the course of the study, based on their baseline blood values and subsequent intake and output. This hypothesis was consistent with previous animal dehydration experiments, which showed the same pattern of relative amplitude decrease exclusively in the muscular tissue during acute dehydration (Li, M. et al. *NMR Biomed.* 28, 1031-1039 (2015)).

Furthermore, some relevant literature shows that non-exercise-based dehydration can lead to a decrease primarily in ECF of the muscle (see, e.g., Costill, D. L. et al. *Metabolic Adaptation to Prolonged Physical Exercise*, H. Howald, J. R. Poortmans, Eds. (Birkhäuser, Basel, 1975), pp. 352-360; and Nose, H. et al. *Jpn. J. Physiol.* 33, 1019-1029 (1983)).

Example 5—Portable NMR Sensor for Bedside Relaxometry Measurements

Figure 5A:
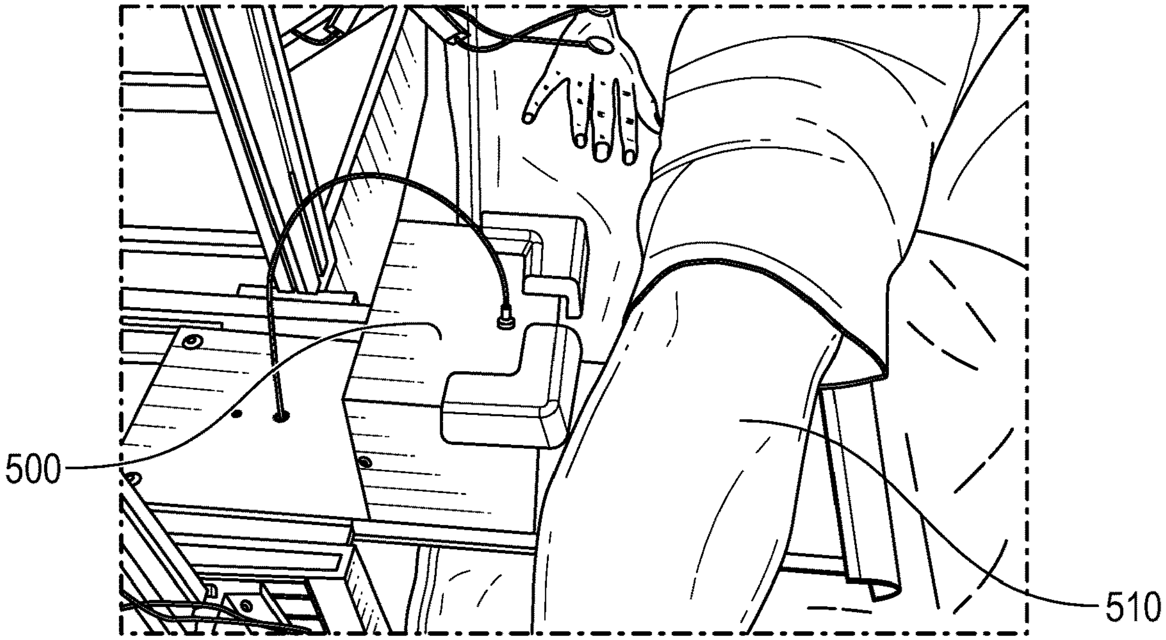
FIG. 5A depicts an embodiment of a sensor placed adjacent a calf muscle.

A custom, single-sided, single-voxel NMR sensor that can be placed against most external soft-tissue parts of the anatomy was used in the examples herein (FIG. 5A). FIG. 5A depicts an NMR sensor 500 arranged adjacent a calf muscle of the upper leg 510 of a subject.

Figure 5B:
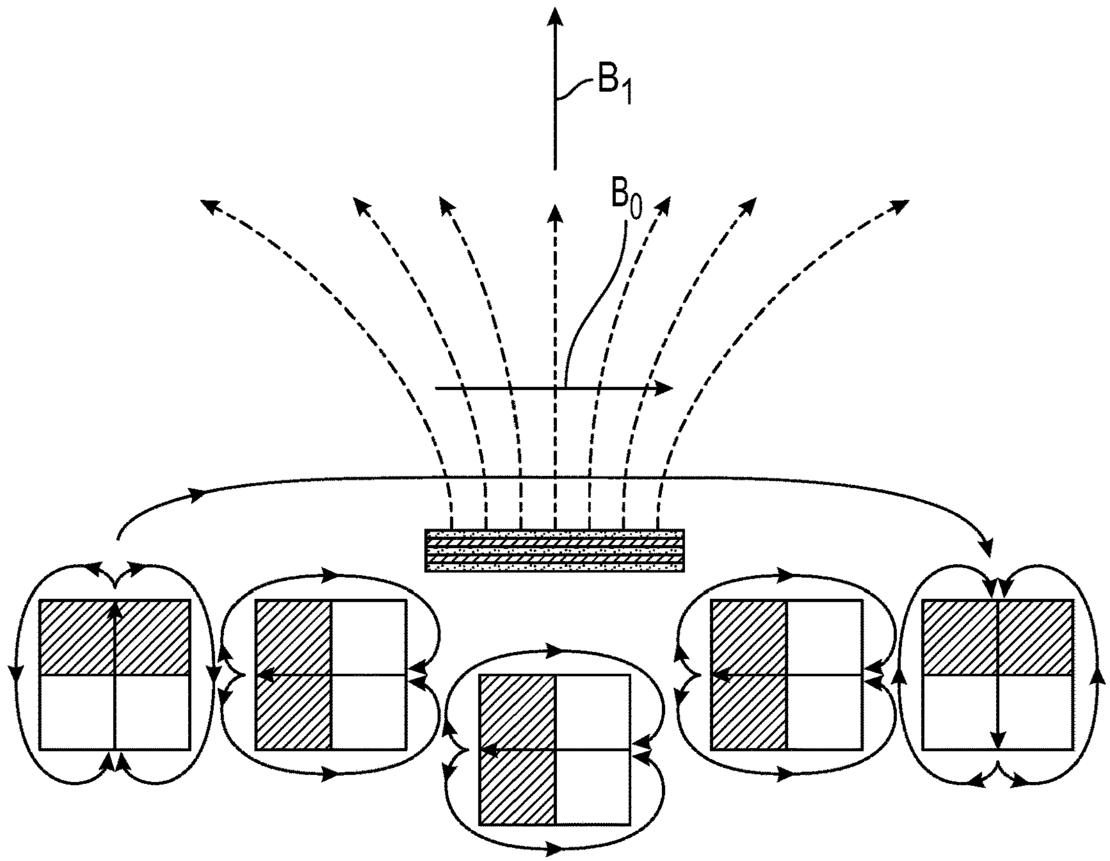
FIG. 5B is a schematic of an embodiment of a linear Halbach design showing magnetization orientation of individual magnets.

The magnet had a 0.28 T main magnet field ($B_0$) created by a unilateral Halbach magnet array, as depicted at FIG. 5B. FIG. 5B is a schematic of a linear Halbach design showing magnetization orientation of the individual magnets as well as the net $B_0$ and $B_1$ orientations. The NMR sensor of the examples herein was able to collect 8000 points in its T2 measurement, compared to the 32 points in the MRI measurement, which allowed the NMR sensor data to be fit by a greater number of exponentials.

Back-to-back T2 relaxation measurements were taken of six phantom and ex-vivo tissue samples with the same MRI and the NMR sensor and pulse sequences as in human measurements in order to understand a suitable way to translate results between the two sensors.

In this example, the phantoms and ex-vivo tissues spanned the T2 relaxation time range that was found in the leg. The NMR and MRI relaxivity measurements had a linear correlation of $r^2$=0.966 (FIG. 6).

Figure 6:
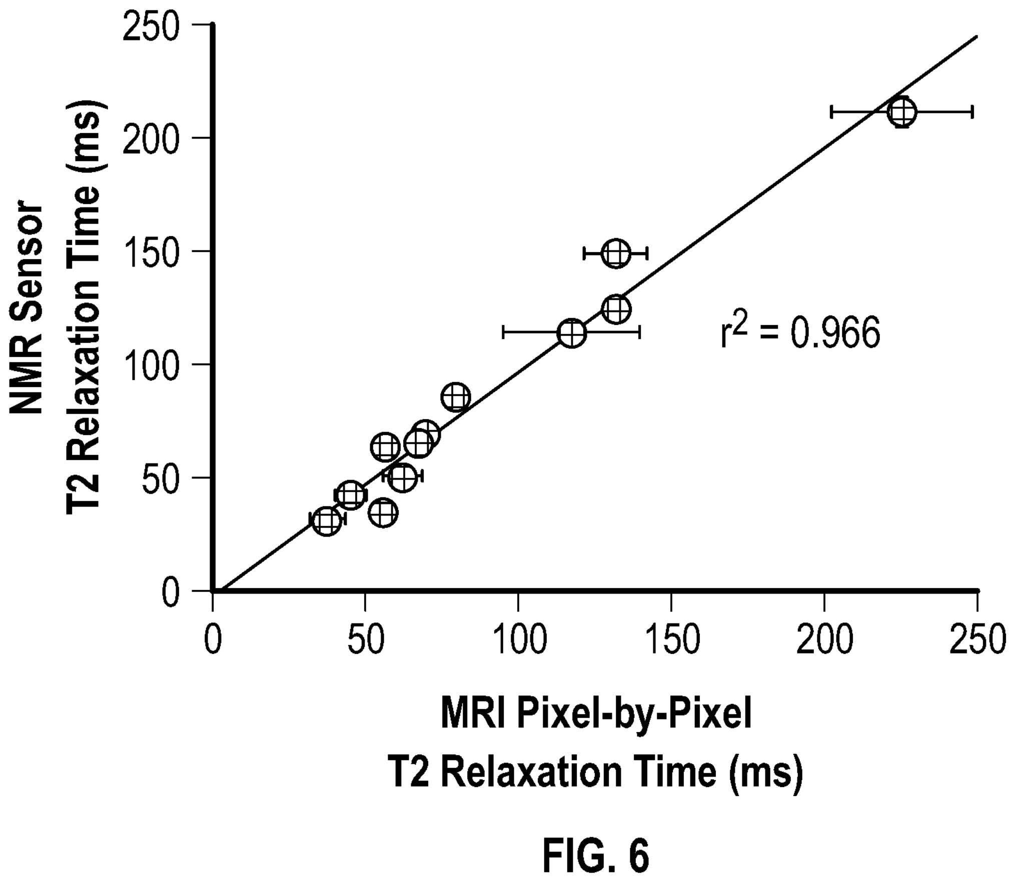
FIG. 6 depicts a comparison of T2 relaxation times collected with an embodiment of a magnetic resonance imaging sensor and an embodiment of a nuclear magnetic sensor.

FIG. 6 depicts a comparison of T2 relaxation times from MRI pixel-by-pixel and NMR sensor. Both mono- and bi-exponential fit results of each of the six phantoms and ex-vivo tissue samples. There was a strong correlation between the MRI and NMR sensor values ($r^2$=0.966), which suggests that the results could be translated between the two sensors. Vertical (NMR sensor) error bars represent the 95% confidence interval for the fit. Horizontal (MRI) error bars represent the standard deviation of the pixel-by-pixel MRI results.

The NMR sensor relaxivity measurements were within 10%, and within 8 ms of the MRI measurements across all sample types, except for the liquid copper sulfate measurement. The NMR sensor had a relatively non-uniform magnetic field compared to the MRI. T2 measurements taken with a particular pulse sequence (e.g., a CPMG sequence) were likely affected by field gradient, inter-echo spacing, and/or the sample's diffusivity.

The larger any of these parameters, the greater the reduction of the measured T2 relaxation time. The aqueous copper sulfate phantom had the largest diffusivity of any of the samples and, therefore, the worst correspondence between MRI and NMR sensor. Also, the aqueous copper sulfate's NMR sensor T2 value was lower than its MRI T2 value. The water diffusivities within tissues were not as large as those of pure water, with the exception of pockets of frank fluid accumulation. Therefore, it was surprisingly discovered that good correspondence occurs between the in vivo MRI and NMR sensor results.

Example 6—Bedside AVR Measurements

The custom NMR sensor of the foregoing example was used to take single-voxel T2 measurements of the same location (upper calf) at the same time points as the MRI measurements (see FIG. 5A).

The NMR sensor's measurement voxel of this example contained skin, subcutaneous tissue, and muscular tissue. The MRI pixel-wise results provided a model with which to analyze a voxel containing these tissues. Both subcutaneous and muscular tissue contained two components (a component is an amplitude and relaxation time pair) as determined by the F test.

The short component, which corresponds to intracellular fluid, had a relaxation time $T_{2,short}$ that overlapped for both tissues. The long component, which relates to ECF, had a relaxation time $T_{2,long}$ that did not overlap between the muscle and subcutaneous tissue (FIG. 2A).

A voxel containing both subcutaneous and muscular tissue, therefore, could include three distinct relaxation times. Advised by the anatomical model and measured correspondence between the relaxation times of the MRI and NMR sensor described herein, these MRI results were utilized to develop a three-exponential model for the NMR sensor data:

$$M(t)_{3exp} = A_a e^{-\frac{t}{T_{2,a}}} + A_b e^{-\frac{t}{T_{2,b}}} + A_3 e^{-\frac{t}{T_{2,c}}},$$

wherein the relative magnitude of the relaxation times was defined as $\tau_1<\tau_2<\tau_3$. Similarly, the relative amplitude of the second relaxation peak, $\tau_2$, was given by—

$$RA_b = \frac{A_b}{A_a + A_b + A_c} \times 100\%.$$

The first exponential, $T_{2,a}$, was consistently observed to be at about 40 ms (FIG. 2A). The third exponential, corresponding to subcutaneous tissue was observed to be from about 200 ms to about 250 ms. $T_{2,a}$ and $T_{2,c}$ were fixed, in this example, to values of 40 ms and 250 ms.

The middle component ($T_{2,b}$, $RA_b$), corresponding to ECF of the muscular tissue, was allowed to float. Thus, the fitted parameters for each relaxivity measurement were $T_{2,b}$, $A_a$, $A_b$, and $A_c$. The amplitude of the middle component ($A_2$, related to ratio of EOF in the muscle) was expected to change in response to dialysis.

Figure 7A:
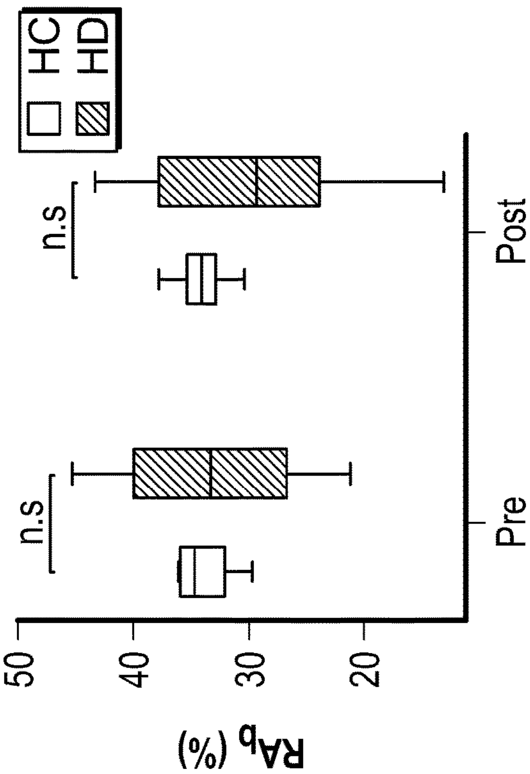
FIG. 7A depicts a boxplot of $RA_b$ values at pre- and post-time points collected from an embodiment of the methods described herein.
Figure 7B:
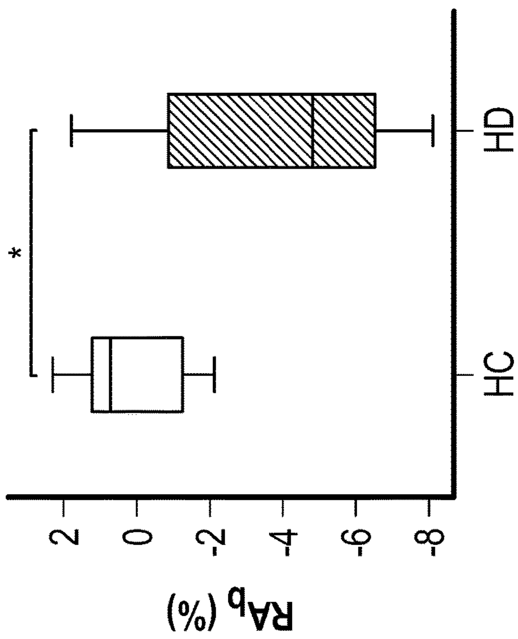
FIG. 7B depicts a boxplot of the change in $RA_b$ for various patients subjected to an embodiment of the methods described herein.
Figure 7C:
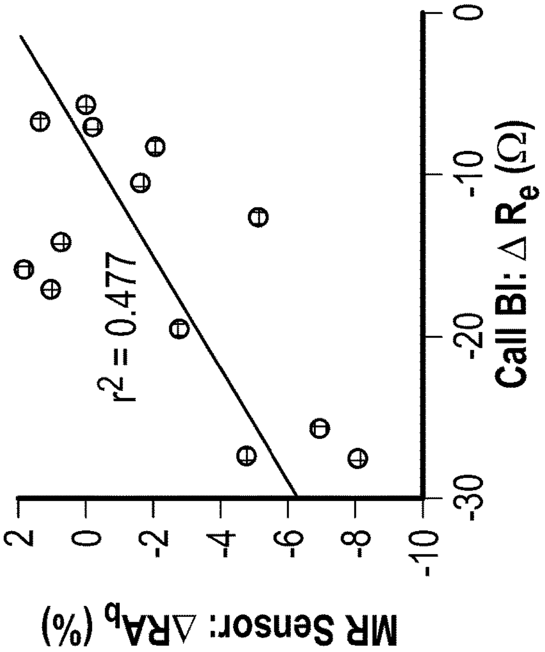
FIG. 7C depicts a plot of the change in $RA_b$ observed as a result of an embodiment of a method described herein.
Figure 7D:
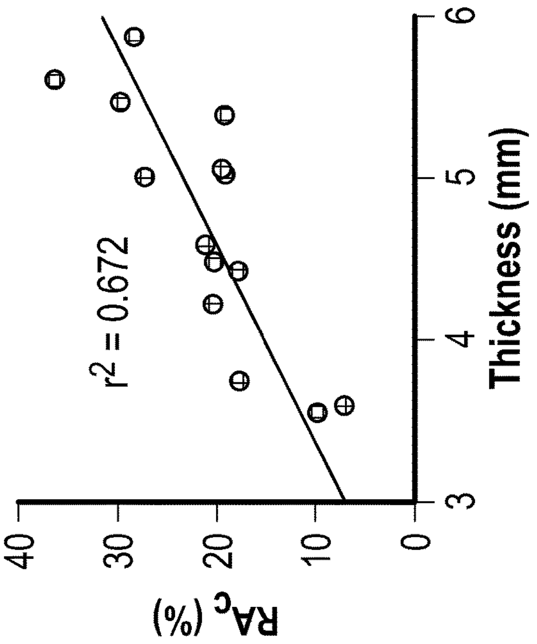
FIG. 7D depicts a plot of $RA_c$ against subcutaneous tissue thickness observed as a result of an embodiment of a method described herein.

FIG. 7A is a boxplot depicting $RA_b$ values at pre- and post-time points, and FIG. 7B is a boxplot depicting the change in $RA_b$ for HC and HD subjects. The central mark in each box plot indicates the median, and the bottom and top edges of the box indicate the 25th and 75th percentiles, respectively. The whiskers extend to the most extreme values not considered outliers. FIG. 7C depicts the change in $RA_b$ plotted against calf bioimpedance's change in ECF-associated resistivity, $R_e$ ($r^2$=0.477). FIG. 7D depicts a plot of $RA_c$ against subcutaneous tissue thickness ($r^2$=0.672). Note that the tissue thickness gets compressed by a few millimeters when the leg is pressed against the NMR sensor for measurement.

The MRI data depicted at FIG. 2A suggested the middle relaxation time should be about 70 ms to about 170 ms. Indeed, the middle relaxation time, $T_{2,b}$, of the NMR sensor data was fit to within the expected range (about 80 ms to about 130 ms). No trends were observed in the relaxation time data of the NMR sensor. The NMR sensor's $R_2$ values, however, decreased significantly more in HD subjects than in HC ones, just as was observed in the MRI data (see FIG. 7B).

This decrease cones ponded to a reduction in the relative volume of ECF in the muscle. The relationship between the change in $RA_b$ and change in ECF resistivity, $R_e$, as measured by calf bioimpedance (BI) measurements at the same time points is depicted at FIG. 7C ($r^2$=0.477). Although bioimpedance does not typically perform well on dialysis subjects, the weak correlation helped to corroborate the observation that the NMR sensor was measuring ECF.

The baseline $RA_b$ values, however, were not statistically significant between HC and HD subjects like they were in the MRI data (FIG. 7A). This likely indicated that the NMR sensor, in this test, was not able to differentiate between euvolemic and fluid-overloaded subjects with a single measurement.

It was hypothesized that the worse performance of the NMR sensor compared to MRI arose from the fact that the constant-volume NMR sensor voxel included variable ratios of subcutaneous tissue to muscle tissue. That ratio should be constant when comparing the pre- and post-measurement for a given patient but can vary between patients. This could be the reason that significance was achieved for pre-to-post changes in $RA_b$ for the sensor, but not between HD and HC groups.

This hypothesis was supported by the fact that the amplitude of the third component (which corresponded to subcutaneous tissue), $RA_e$, and the thickness of subcutaneous tissue for each patient were correlated at the level of $r^2$=0.67 (FIG. 7D). A greater subcutaneous tissue thickness indicated that subcutaneous tissue occupied a greater portion of the sensor voxel.

Also explored was the minimum voxel size and a location that an NMR sensor could measure in order to distinguish euvolemia from volume overload with a single measurement. Several small ROIs were drawn in multiple different locations in the upper calf (FIG. 7D).

The average T2 decay curves of each ROI were analyzed with bi-exponential decay curves. The results of the small ROIs were summarized by analyzing an MRI scan, which showed the size and location of the some of the smaller ROIs.

A 0.5 $cm^3$ voxel (1 cm×1 cm×0.5 cm) within the anterior (p=0.0198) or lateral (p=0.0091) muscle groups was sufficient to detect fluid overloaded subjects with a single measurement. If the 0.5 $cm^3$ voxel was split between muscle and subcutaneous tissue, however, the measurement of this example was not able to distinguish between euvolemic HCs and hypervolemic HDs. In such instances, more muscle tissue could be measured in order to distinguish fluid overload from euvolemia with a single measurement. These results provided a minimum volume, penetration depth, and anatomical measurement location, which may inform NMR sensor designs. Possible methods for designing a sensor that may meet these volume and penetration depth requirements have been outlined (see, e.g., Bashyam, A. et al. *J. Magn. Reson.* 9, 36-43 (2018)).

Table 3 depicts a summary of P values comparing HC and HD subjects for each small ROI of this example.

TABLE 3

Summary of P Values

| | AM | PM | Change |
|---|---|---|---|
| Lateral: Subcutaneous + Muscle | 0.310 | 0.130 | 0.125 |
| Lateral: Only Muscle | 0.02* | 0.104 | 0.021* |
| Anterior: Subcutaneous + Muscle | 0.082 | 0.498 | 0.0308* |
| Anterior: Only Muscle | 0.027* | 0.191 | 0.0239* |

P-values were calculated by a two-sample permutation test with Monte Carlo estimation using $10^5 - 1$ repetitions.
*signifies $p < 0.05$.

Example 7—Bioimpedance Measurements

Bioimpedance (BI) typically cannot distinguish between hypervolemic HD and euvolemic HC subjects with a single measurement. Raw BI resistance values are summarized in FIGS. 8A-H.

Figure 8A:
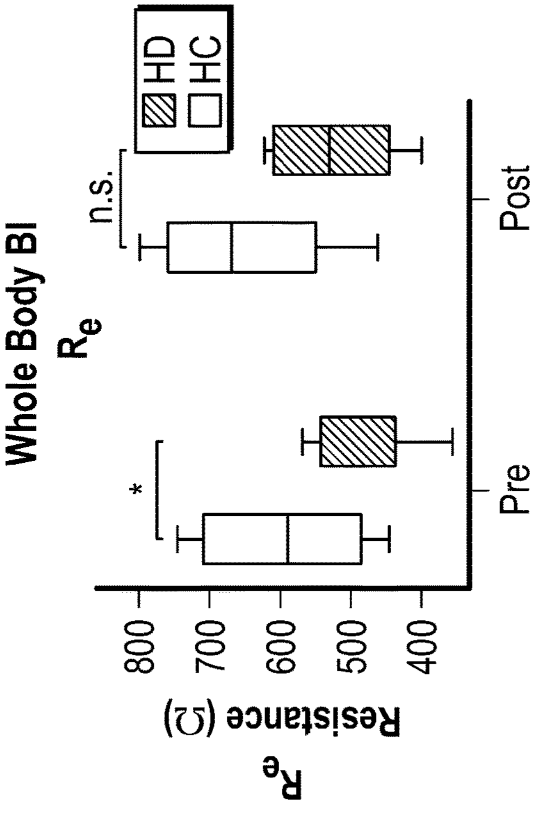
FIG. 8A depicts raw resistivity measurements collected from a whole body according to one embodiment of the methods provided herein.
Figure 8B:
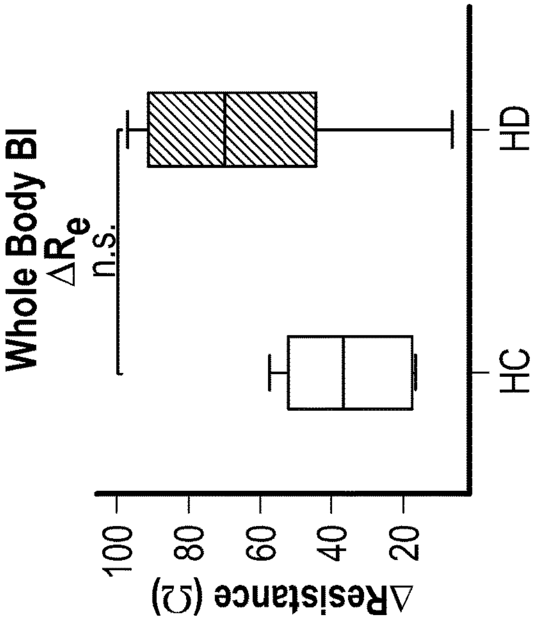
FIG. 8B depicts raw resistivity measurements collected from a whole body according to one embodiment of the methods provided herein.
Figure 8C:
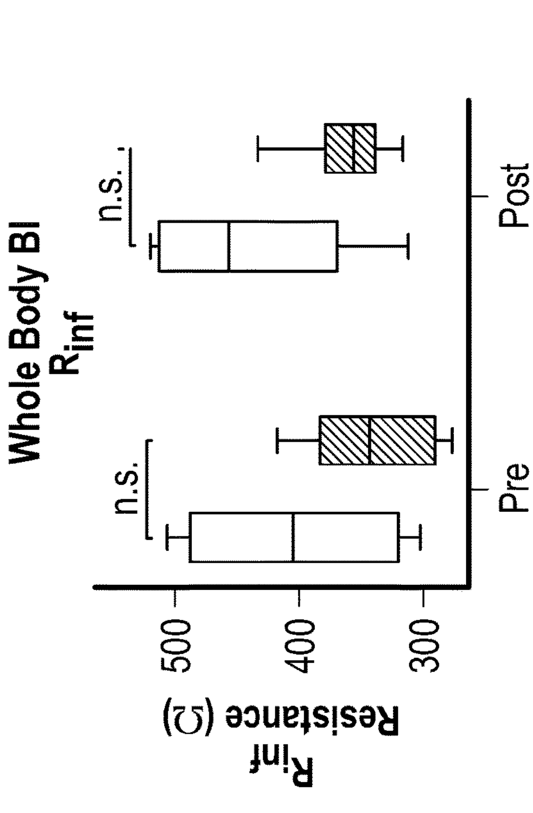
FIG. 8C depicts raw resistivity measurements collected from a whole body according to one embodiment of the methods provided herein.
Figure 8D:
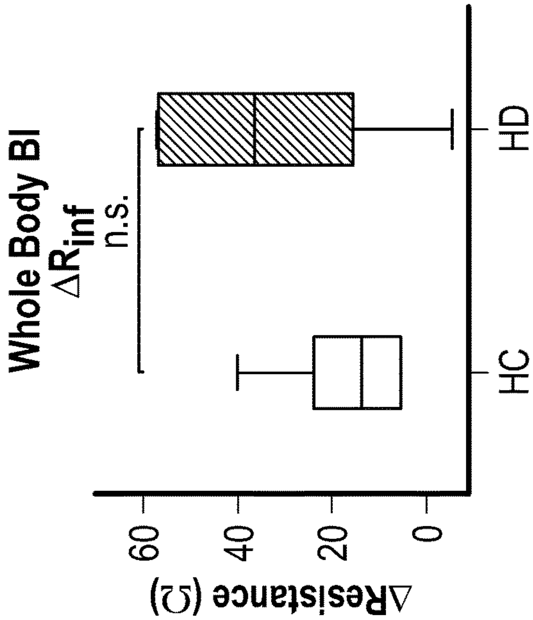
FIG. 8D depicts raw resistivity measurements collected from a whole body according to one embodiment of the methods provided herein.
Figure 8E:
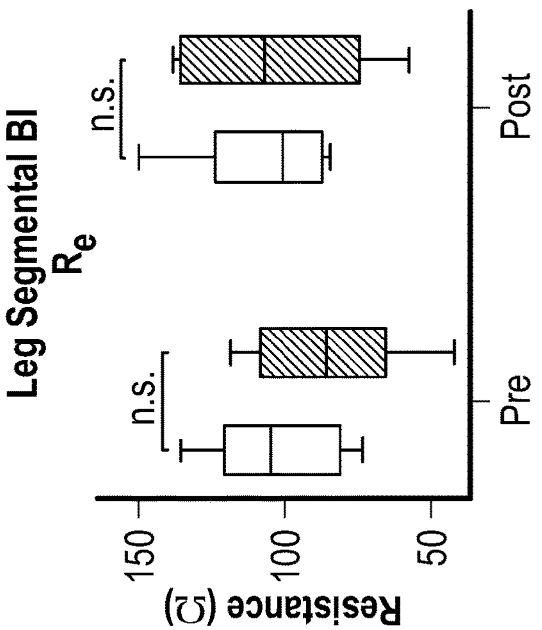
FIG. 8E depicts raw resistivity measurements collected from a leg according to one embodiment of the methods provided herein.
Figure 8F:
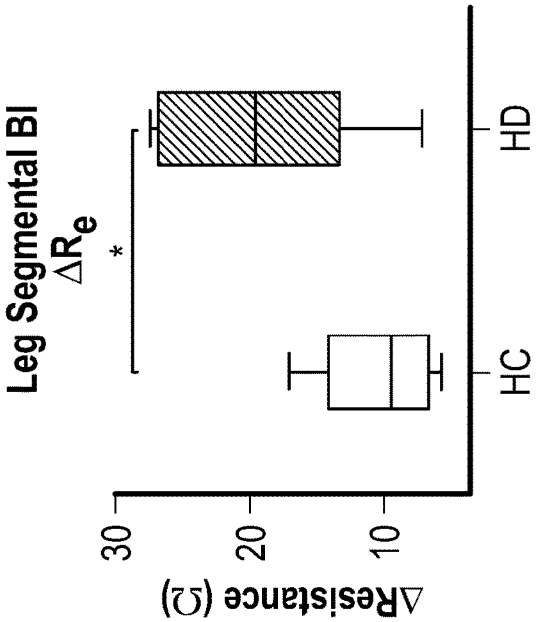
FIG. 8F depicts raw resistivity measurements collected from a leg according to one embodiment of the methods provided herein.
Figure 8G:
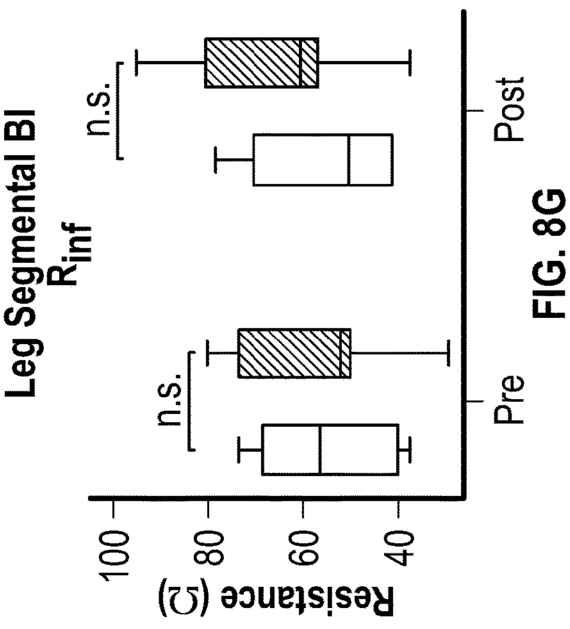
FIG. 8G depicts raw resistivity measurements collected from a leg according to one embodiment of the methods provided herein.
Figure 8H:
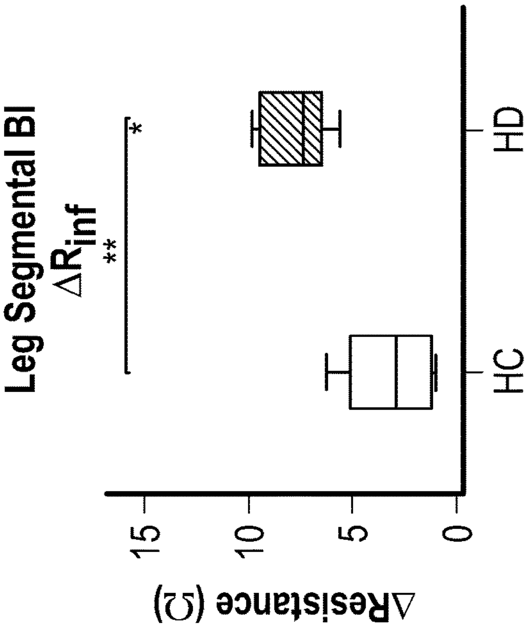
FIG. 8H depicts raw resistivity measurements collected from a leg according to one embodiment of the methods provided herein.
Figure 8I:
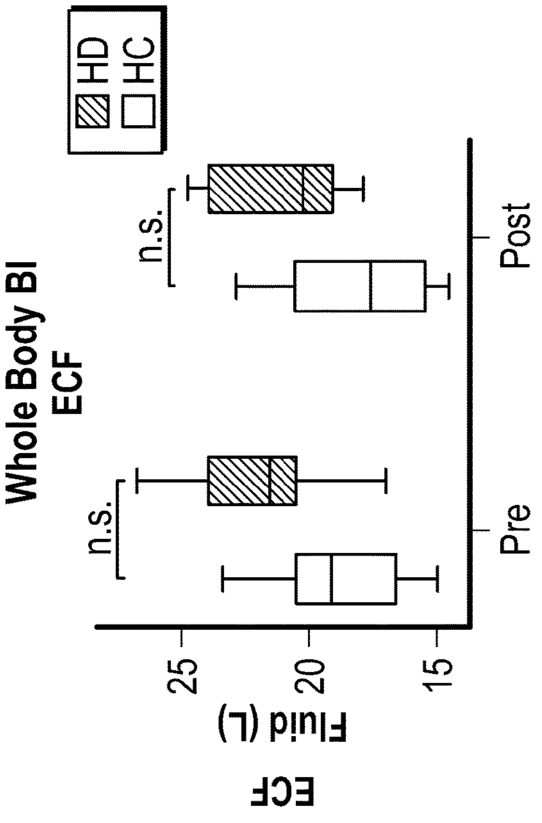
FIG. 8I depicts total body water and extracellular fluid space bioimpedance measurements collected from a whole body according to one embodiment of the methods described herein.

FIGS. 8A-D depict data collected from whole body bioimpedance measurements, whereas FIGS. 8E-H depict data collected from segmental leg bioimpedance measurements. FIG. 8A, FIG. 8B, FIG. 8E, and FIG. 8F show $R_e$ data, which corresponded to ECF. FIG. 8C, FIG. 8D, FIG. 8G, and FIG. 8H show $R_{inf}$ data, which corresponded to TBW. Fluid has a low resistivity. Low resistivity indicates mare fluid. Higher resistivity indicates less fluid. An increase in resistivity indicates decrease of fluid. For this data, it was only possible to distinguish HD from HC subjects at a single time point with a whole body $R_e$ measurement at baseline (FIG. 8A). FIGS. 8F and 7H include data demonstrating that it was possible to distinguish HD from HC subjects based on the change in $R_e$ and $R_{inf}$ in the leg.

The whole body $R_e$ measurement was able to distinguish between the two populations with a single measurement at baseline (p=0.02). None of the leg BI measurements was able to do so. Whole body BI measurements were not able to distinguish significantly between the change in volume status that accompanied dialysis treatments as compared to the stable volume status of healthy controls.

Both segmental leg measurements were able to do so ($\Delta$Re: p=0.03, $\Delta R_{inf}$: p=0.002). The extracellular fluid (ECF) and total body water (TBW) volumes obtained by inserting the raw BI resistance values into predictive equations are summarized in FIGS. 8I-P.

FIGS. 8I-L depict data collected from whole body bioimpedance measurements, whereas FIGS. 8M-P depict data collected from segmental leg bioimpedance measurements. FIG. 8I, FIG. 8J, FIG. 8M, and FIG. 8N depict ECF data. FIG. 8K, FIG. 8L, FIG. 8O, and FIG. 8P depict TBW data. For this data, it was possible to distinguish significantly HC from HD subjects based on the change in whole-body ($p=0.027$) or leg ($p=0.014$ with permutation test; $p=0.054$ with Welch test) ECF.

Figure 8J:
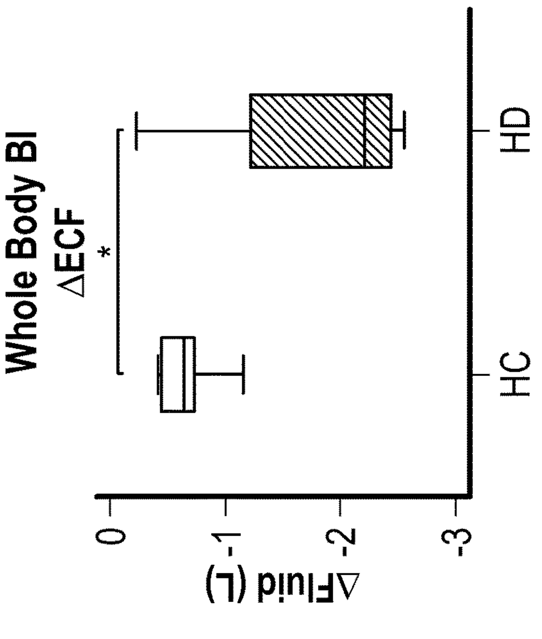
FIG. 8J depicts total body water and extracellular fluid space bioimpedance measurements collected from a whole body according to one embodiment of the methods described herein.
Figure 8K:
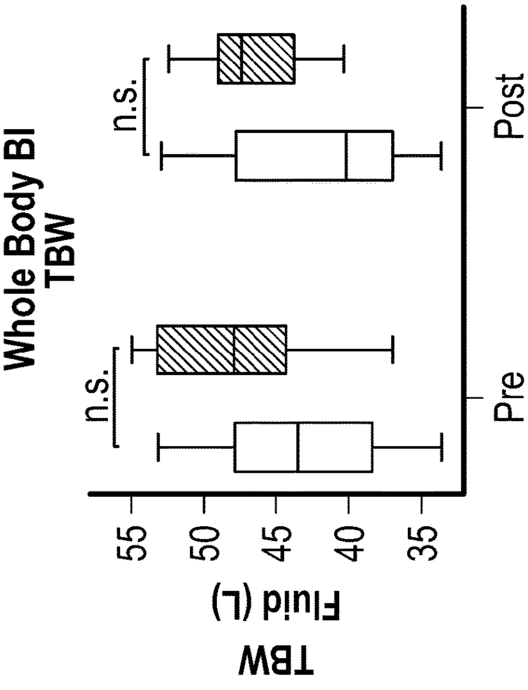
FIG. 8K depicts total body water and extracellular fluid space bioimpedance measurements collected from a whole body according to one embodiment of the methods described herein.
Figure 8L:
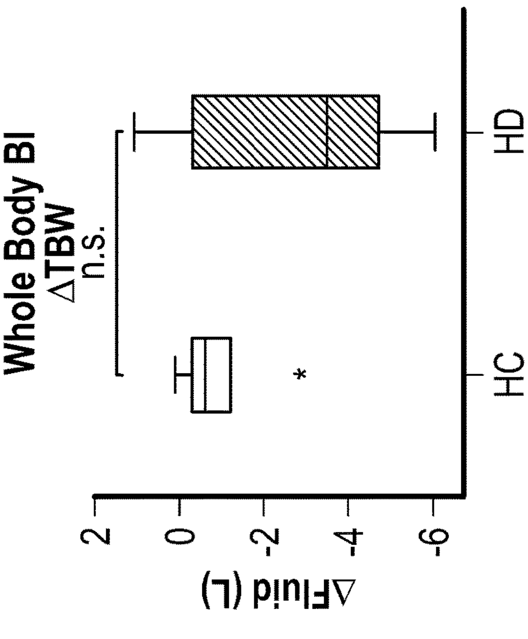
FIG. 8L depicts total body water and extracellular fluid space bioimpedance measurements collected from a whole body according to one embodiment of the methods described herein.
Figure 8M:
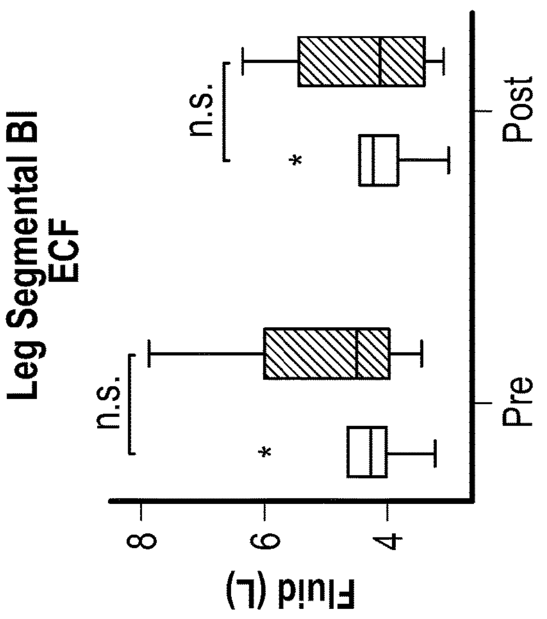
FIG. 8M depicts total body water and extracellular fluid space bioimpedance measurements collected from a leg according to one embodiment of the methods described herein.
Figure 8N:
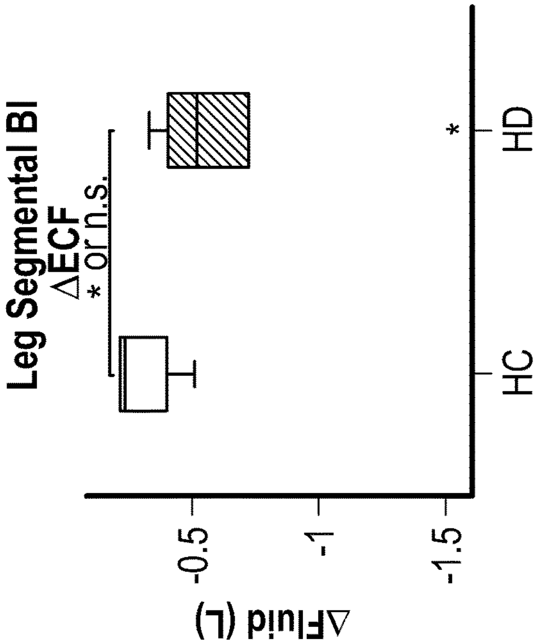
FIG. 8N depicts total body water and extracellular fluid space bioimpedance measurements collected from a leg according to one embodiment of the methods described herein.
Figure 8O:
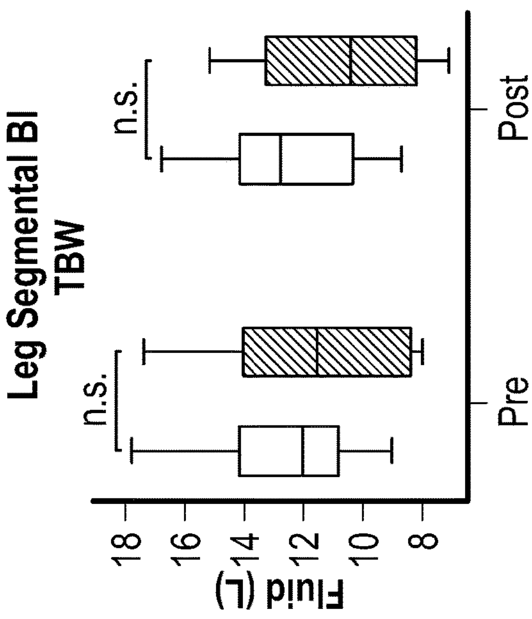
FIG. 8O depicts total body water and extracellular fluid space bioimpedance measurements collected from a leg according to one embodiment of the methods described herein.
Figure 8P:
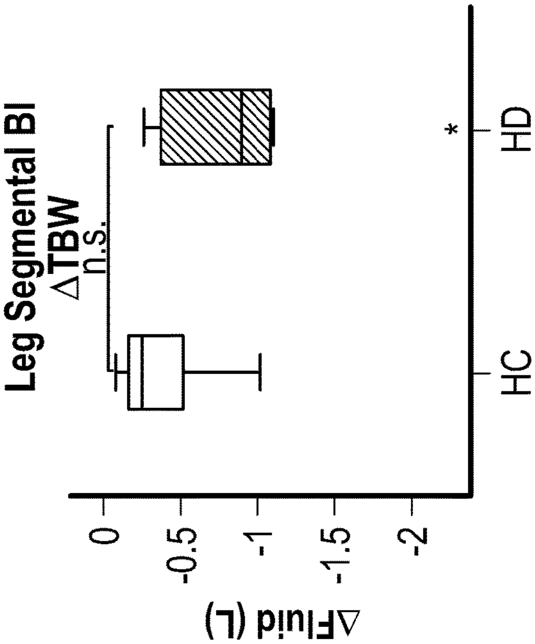
FIG. 8P depicts total body water and extracellular fluid space bioimpedance measurements collected from a leg according to one embodiment of the methods described herein.

Statistics were calculated with both a Welch test and permutation test for all plots depicted at FIGS. 8A-P. The significance level was the same for both statistical tests across all plots, except for the subplot at FIG. 8N, where the permutation test was significant, but the Welch test was not (n.s. indicates $p>0.05$, *indicates $p<0.05$, **indicates $p<=0.01$).

Bioimpedance's ability to distinguish statistically significantly between euvolemic HCs and hypervolemic HDs when volume equations were applied decreased across most measurements types, except for the change in whole body ECF (FIG. 8J).

The findings of the foregoing examples suggested that bedside NMR measurements may be a safe, non-invasive method to identify fluid overload and, therefore, inform therapy in ESRD patients (e.g., guide dry weight determination), and potentially other patient populations (e.g., titrate diuretics in heart failure) to attain euvolemia with greater clinical efficacy.

NMR may have one or more benefits over other fluid-monitoring modalities. Continuous blood volume monitoring measures only relative blood volume changes, which can help reduce hypotensive episodes during dialysis, but typically cannot tell if a subject has attained their dry weight or has residual fluid overload. Bioimpedance (BI) may be affected by factors such as sweat, electrode placement, body shape assumptions, and/or the validity of population-specific equations, whereas NMR intrinsically measures water molecules. In a head-to-head comparison of BI to magnetic resonance, BI measurements generally performed worse than MRI and comparably to the NMR sensor.

The body resistance measured by low-frequency current from wrist-to-ankle electrodes—$R_{e,\ whole\ body}$—was a BI measurement that was able to distinguish significantly between the NC and HD groups with a single, baseline measurement. The statistical significance, however, was lost when the raw $R_e$ resistance values were inserted into an FDA-approved equation to estimate ECF volume. The bioimpedance device that was utilized was FDA-approved for estimating whole-body composition—including TBW and ECF—for healthy individuals with normal fluid physiologies. The loss of significance when converting from $R_e$ to ECF likely resulted from inserting data from dialysis patients into algorithms developed on euvolemic, healthy volunteers. Among the benefits of NMR over BI include the fact that it inherently measures fluid volume (a benefit that is harnessed by the oil and food quality control industries) without relying on population-specific equations and assumptions about body shape.

Example 8—Experimental and Study Details, and Equipment

The tests of the foregoing examples were performed according to the following procedures and equipment.

The study day began and ended with MRI scans and consisted of dialysis HD subjects) or bedrest (for HC subjects) in between the two scans.

HD patients received their usual hemodialysis treatment (about 3 to about 4 hours) in a hospital bed (in a reclined supine position with legs outstretched). The ultrafiltration volume was prescribed by the study nephrologist. HCs sat on the same hospital bed for 4 hours. All subjects were given the option of a to-go snack before returning for the second MRI. All intake and output was recorded for each participant during the 4-hour study interval.

Pre- and Post-Measurements: The following, set of measurements was taken for every study participant at the start and end of dialysis or bedrest: a standing weight, blood work (details below), baseline $T_2$ measurements of the upper calf contralateral to HD's access site (right leg for HCs) with the single-sided NMR sensor (the same anatomical location that was measured with the MRI), and bioimpedance measurements of the whole body wrist-to-ankle electrode placement) and calf segmental (upper calf-to-lower calf electrode placement).

Blood Work: All subjects had blood drawn at the beginning of the 4-hour study interval following the first MRI. The laboratory work that was collected included the following: serum sodium, blood urea nitrogen (BUN), creatinine, complete hemoglobin and hematocrit, serum osmolality, and B-type natriuretic peptide (proBNP). HDs also had routine pre- and post-dialysis labs as dictated by the hospital's dialysis unit protocols, and a sample of blood collected for storage in a biorepository.

MRI Scans: MRI scans of the upper calf were obtained on a 1.5 T SIEMENS® AVANTO® scanner (SYNGO® MR B17 software) and CP extremity coil.

The upper calf (right leg for HCs leg contralateral to dialysis access site for HDs) was positioned at the center of the extremity coil using padding when necessary. A localizing capsule was placed on the lateral aspect of the widest part of the calf (MR-SPOT® 121 marker, Beekley Medical Corp., Bristol, CT).

An initial set of localizing MRI scans were performed to find the location of the capsule (Scanning Sequence/Variant: GR/SP (fl2d1), Repetition Time (TR): 7.7 ms, Echo Time (TE): 3.2 8 ms, Flip Angle (FA): 20°, Thickness: 6 mm, 3 slices in each anatomical direction).

A quantitative multi-echo spin echo T2 scan (se2d32) was performed with parameters TR 3300 ms, TE 8 ms, 32 echoes, 1 average, 4 sagittal slices of 5 mm thickness with 60% spacing (3 mm) between slices, 192×144 matrix (75% phase field-of-view), 1×1 mm in-plane pixel resolution, and a total acquisition time of 7 minutes 53 seconds. The sagittal scans were positioned such that the localizing capsule appeared in every slice.

MRI Analysis: Software: The raw DICOM (Digital Imaging and Communications in Medicine) images from the scanner were converted to NIfTI (Neuroimaging Informatics Technology Initiative) format with FreeSurfer software, regions of interest (ROIs) were hand-drawn on each slice of each scan using FSLeyes image viewer (and the older version, FSLview image viewer), and all further analysis was performed in MATLAB® 2017b analysis software.

The hand-drawn ROIs were (1) Subcutaneous Tissue, which includes skin, fat and blood vessels in the fat, (2) Bone and Marrow, both of which include tibia and fibula, (3) Muscular Tissue, which includes muscle, fascia, nerves, and blood vessels, and (4) Whole Leg, which includes all of the aforementioned tissues. ROIs of sub-muscles were drawn on the first slice of each scan and included the following: gastrocnemius (includes both medial and lateral heads), soleus, deep posterior (includes flexor hallucis longus, tibialis posterior, flexor digitorum longus), anterior (includes tibialis anterior, extensor halluces longus, extensor digitorum longus), and lateral (includes peroneus brevis and peroneus longus).

MRI Analysis: Pixel-wise: The quantitative T2 MRI images were analyzed by fitting each pixel on each slice with a mono- and bi-exponential decay. An F test was utilized to determine the optimal model for pixels within each tissue type, which showed that a bi-exponential fit was optimal for all tissue types except for bone. The initial point of the T2 decay was ignored due to lack of stimulated echo effects. There were a total of 31 points from 16 ms to 256 ms with 8 ms spacing that were fit to the following equations:

$$M(t)_{1exp} = A_{1exp} e^{-\frac{t}{T_{2,1exp}}}$$

$$M(t)_{2exp} = A_{short} e^{-\frac{t}{T_{2,short}}} + A_{long} e^{-\frac{t}{T_{2,long}}}$$

The starting values used for the bi-exponential fit were [$A_{short}$=1500, $T_{2,short}$=50, $A_{long}$=1500, $T_{2,long}$=210]. The upper and lower limits for the fittings were set to 10,000 and 0. Non-linear least squares fitting method was used with a Trust-Region algorithm to perform the fits using MATLAB® 2017b analysis software.

Pixel fit results were deleted if any of the following criteria ere met: (1) the root mean squared error (RMSE) of the pixel fit was greater than the $99^{th}$ RMSE percentile for that scan, (2) either of the two relaxation times was less than 0.5TE=4 ms, (3) either of the two relaxation times was greater than the maximum T2 that could be expected to be measured with less than 5% relative error (calculated by the empirically-derived expression 25.63*SNR+197.6), (4) the 95% confidence interval of any parameter was fit to NaN, or (5) the difference between the two relaxation times was less than 10 ms.

The cumulative distribution function (cdf) plots of the pixel-wise data visually showed the percentage of pixels that was below a particular value. The pre-to-post change for pixel-wise data was calculated by (1) subtracting the pre- and post-cdfs from each other (i.e. HC difference cdf=HC pre cdf−NC post cdf) and (2) integrating across the difference cdf curve (FIG. 3D, for example, is the integral of the difference cdf).

MRI Analysis of ROI: The T2 decay of each pixel within an ROI was averaged together. A mono- or bi-exponential fit was then performed on the average 31-point (because $1^{st}$ point was ignored) decay for that ROI according to the same specifications described in the pixel-wise section above.

Skin and Subcutaneous Thickness Measurements: The skin and subcutaneous tissue, thicknesses were calculated from the MRI localizing scans using the length measurement tool on the software program OSIRIX® Lite DICOM viewer (Pixmeo SARL, Bernex, Switzerland). The thickness of the skin and subcutaneous tissue was measured in 4 locations around the localizing marker on each of the 3 sagittal localizer slices for both pre- and post-scans. All 24 skin and all 24 subcutaneous thickness values were averaged together to obtain the average skin and subcutaneous thickness for a particular subject. Note that the skin and subcutaneous tissue thickness traversed by the NMR sensor was less than the values measured with this method. The subcutaneous tissue was compressed by a few millimeters during data collection when the leg was pressed against the NMR sensor.

NMR Sensor—Clinical Set-up: The NMR sensor was attached to the platform of a custom aluminum cart that extended onto the patient's bed. The subject's pant leg was rolled up and their calf was put directly on the aluminum platform for grounding and directly against the surface of the sensor coil (FIG. 5A). The cart position was adjusted such that the spot where the MRI localizing marker was placed touched the NMR sensor coil. Subjects were instructed not to move their leg for the duration of the NMR measurement and data collection was re-started if patients moved.

Ambient and magnet temperatures were recorded throughout the dialysis session with a continuous temperature logger and K-type thermocouples (RDXL4SD thermocouple, OMEGA Engineering, USA). A phantom filled with an aqueous solution of copper sulfate of known T2 relaxation time was taken before and after each human measurement so that any sensor malfunctions could be immediately identified. Ambient temperatures tended to rise throughout the study due to the body heat of the study subject, and possibly the study staff sitting in a small hospital room. The measured T2 of the phantom, however, did not change by more than 2.8 ms (an outlier that occurred once). The average pre-to-post change in measured phantom T2 value was, in fact, much smaller at 0.84±0.78 ms. This phantom validation step ensured that the sensor was functioning properly and measured consistent T2 values throughout the study.

NMR Sensor: Hardware: A custom single-sided, sweet-spot NMR sensor for the study of these examples was produced that could be placed against most external soft-tissue parts of the body. The magnet had a 0.28 T main magnetic field ($B_0$) created by a unilateral linear Halbach design (Bashyam, A. et al. *J. Magn. Reson.* 9, 36-43 (2018)). 150 cuboidal neodymium iron boron (NdFeB, N52 grade) magnets (Viona Magnetics, New York, USA) were positioned across 5 slabs in a 5×6 grid within each slab. The magnets were placed in the 5×6 grids with their magnetization orientations pointing in a different direction based on which slab they were in. The sensor measured approximately 3.5×3.5×6 inches and weighed approximately 12 pounds.

The magnet's "sweet spot" region had a saddle shape, wherein the $B_0$ field was approximately 80 $mm^3$ (4×5×4 mm) in volume at 0.281 field strength. The transmit-receive coil was a single circular solenoid coil approximately 1.6 cm in diameter tuned to 11.61 MHz.

The custom magnet was connected to a Kea2 spectrometer with dual transmit channels 1-100 MHz and duplexer/pre-amplifier module from 7-16 MHz (Magritek, Ltd., Wellington, New Zealand and Aachen, Germany).

NMR Sensor—Pulse Sequences: The $T_2$ relaxation times were measured using a CPMG sequence. Prospa software was utilized to run various pulse sequences (Magritek, Ltd., Wellington, New Zealand and Aachen, Germany). The $T_2$ measurements were taken with a CPMG sequence with 8000 echoes, 65 us echo time, 3 dummy echoes, 12 us pulse length, 16 points per echo, 0.5 us dwell time, 2000 kHz bandwidth, 800-3500 ms inter-experimental delay, autophasing, 8 averages per measurement, and 11.61 Mz $B_1$ frequency. Hard 90- and 180-degree pulses were used (−12 dB and −6 dB pulse attenuation, respectively) and phase cycling was performed. 8 averages were taken per measurement, and 3-10 measurements per time point that were then averaged together in the post-processing analysis.

NR Sensor—Data Analysis: The $T_2$ decays from each time point were averaged together using a straight-averaging technique. The first point was deleted from the averaged decay. The averaged decay was plotted for a representative HC and HD subject. The average SNR of all subjects across all time points was 80.4±24.5 (mean±std). SNR was calculated as the ratio of the maximum value of T2 decay divided by the standard deviation of the noise floor at the end of the T2 decay. The decay signal was fit to a three-exponential decay based on the model developed through the MRI pixel-by-pixel results. The NMR sensor data was forced to fit to a 3-exponential decay, wherein the first exponential was fixed at 40 ms, the third exponential was fixed at 250 ms, and all other parameters were allowed to float.

$$M(t)_{3exp} = A_a e^{-\frac{t}{40ms}} + A_b e^{-\frac{t}{T_{2,b}}} + A_c e^{-\frac{t}{250ms}}$$

The starting values used for the fit were [$A_a$=9, $A_b$=5, $A_c$=7, $T_{2,b}$=100]. The lower and upper limits for the fittings were set to 0 and infinity, respectively, for the amplitudes, and 0 and 250 for relaxation time 2. A non-linear least squares fitting method with a Trust-Region algorithm was used to perform the fits using MATLAB® 2017b analysis software (Mathworks, Inc., Natick, MA).

Phantoms and Ex Vivo Tissues: Three phantoms—vegetable oil, agar, copper sulfate (CuSO4; Sigma-Aldrich, Missouri, USA)—and three ex-vivo tissue samples—muscle (bovine), fat (porcine), and skin (porcine)—were measured with the MRI and NMR sensor protocols described above for human subjects. The copper sulfate was diluted with deionized water to ensure a longer relaxation time. The ex-vivo tissues were kept in a sealed petri dish to avoid dehydration over time as much as possible. The agar-based phantom was made by a protocol from the literature (Hattori, K. et al. *Med Phys* 49, 032303-1:11 (2013)).

Bioimpedance—Setup: Bioimpedance (BI) spectroscopy measurements were taken with an IMP™ SFB7 unit and dual-tab body composition electrodes (ImpediMed, Ltd., Australia). The system used a single channel tetra-polar configuration and performed a frequency sweep of 256 frequencies from 10 to 500 kHz. The IMPEDIMED BIOIMP® software (version 5.4.0.3) was used to apply Cole analysis and Hanai mixture theory to the raw data. For whole-body BI measurements, the two dual-tab electrodes were placed at the wrist and ankle of the side of the body contralateral to the dialysis patient's access (right side for HCs). For the calf segmental BI measurements, the two dual-tab electrodes were placed at the lateral aspect of the calf at the same side of the body. The distance between the two calf electrodes and the calf length (from fibula head to the lateral malleolus) was recorded.

Bioimpedance—Analysis: Three BI measurements were taken at the pre- and post-time points and results were averaged together. If any of the resistance values fit by the model were zero, the trial was excluded from the average. The $R_e$ (modeled zero-frequency resistance, correlated to ECF), $R_{inf}$ (modeled infinite-frequency resistance, correlated to TBW), and whole body TBW and ECF values were taken directly from the IMPEDIMED BIOIMP® software (FDA-approved for healthy, euvolemic individuals). The leg segmental TBW and ECF values were manually calculated based on the following equations published in the Hydra Model 4200 Manual (55):

$$ECF = \frac{\rho_{ECF}^{2/3}}{3*(4\pi)^{1/3}*1000} * L * \left(C_1^2 + C_1^2 + C_1 C_2\right) * \left(\frac{L}{C_1 C_2 R_E}\right)^{2/3}$$

$$\left(1 + \frac{ICF}{ECF}\right)^{5/2} = \left(\frac{R_E + R_I}{R_I}\right)\left(1 + \frac{k_\rho ICF}{ECF}\right)$$

-continued $$k_\rho = \frac{\rho_{ICF}}{\rho_{ECF}}$$

$$TBW = ECF + ICF$$

wherein ECF is the predicted segmental extracellular fluid volume (L); ICF is the predicted segmental intracellular fluid volume (L); $\rho_{ECF}$ is the resistivity of the extracellular fluid (Ω*m), 273.9 Ω*m for males, and 235.5 Ω*m for females (Resistivity values provided by ImpediMed, Inc.); $\rho_{ICF}$ is the resistivity of the intracellular fluid (Ω*m), 937.2 Ω*m for males, and 894.2 Ω*m for females (Resistivity values provided by ImpediMed, Inc.); L is the calf length (cm); C1 is the calf circumference (cm); C2 is the calf circumference (cm); $R_E$ is the resistance value from the model fitting (Ω); and $R_I$ is the resistance value from the model fitting (Ω).

The reported $ECF_{leg\ segmental}$ and $TBW_{leg\ segmental}$ values were calculated using calf length, rather than electrode spacing because electrode spacing was not recorded for subject HC3.

Statistical Analyses: Statistical tests were calculated in MATLAB® 2017b analysis software (Mathworks, Inc., Natick, MA) and RStudio (RStudio, Inc. Boston, MA). All tests were two-sided and a p value of <0.05 was considered statistically significant.

Comparison of HC and HID groups (two-sample): The significance between values for HC and HD groups was compared using both a Welch test and a permutation test. Using either p value did not change the conclusions presented in the paper. The permutation test was more appropriate given the small sample size (n=14). The Welch Test was a two-sample, two-sided t-test with unequal variances. The Satterthwaite's approximation was used to calculate the effective degrees of freedom. The Permutation Test (two-sample) was a two-sample permutation test using Monte Carlo method with $10^5$-1 replications.

Comparison of a single group at two time points aired): When comparing the same subject group at two different time points (i.e., HC pre vs HC post), both a paired Student t-test and a one-sample permutation test were used on the difference (i.e., diff=HC_pre–HC_post): Permutation Test (one-sample): Fisher's one-sample permutation, two-sided test with $10^5$ permutations; Paired t-Test: paired, two-sided Student t-test.

Quantile regression of pixel-wise MRI results: A quantile regression with clustering was performed on the pixelwise MRI results to quantify the difference between HC and HD groups at each time point (i.e., FIG. 3B, FIG. 3C, and FIG. 3D). The Quantile Regression with Clustering was aquantile regression with wild bootstrap method proposed in the literature (Feng, X et al. *Biometrika* 98, 995-999 (2011)) to estimate standard errors given that the data has clustered responses (each subject has data from many pixels, which are not independent).

Determination of optimal model for T2 data fining: The extra sum-of-squares F-test, or simply F-test, was utilized to determine the optimal number of exponentials that should be used to model the $T_2$ data. The test compared two nested models where one model was a simpler version (i.e., certain parameters are set to zero) of the other. The relationship between the relative increase in sum-of-squares and relative increase in degrees of freedom was expressed as an F ratio:

$$\text{Sum of Squares} = SS = \sum_{i=1}^{n} (y - y_i)^2$$

-continued $$F \text{ ratio} = \frac{(SS1 - SS2)/SS2}{(DF1 - DF2)/DF2}$$

wherein y is the true value of the data, yi is the value predicted by the model, and DF, or degrees of freedom, is defined as n−m, wherein n is the number of data points and m is the number of parameters in die model. The more complex model was defined as model 2 and the simpler model was model 1. The p-value was obtained from an F distribution look-up table. The null hypothesis was that the simpler model was correct. The p-value threshold was set to 0.05.

We claim:

1. A method for determining a fluid volume status of a patient, wherein the patient's fluid volume includes the patient's blood volume, interstitial fluid volume, and intracellular fluid volume, and wherein the fluid volume status is hypovolemic, euvolemic, or hypervolemic, the method comprising:

(a) measuring a quantitative relaxation time (T2) of a muscle of the patient, wherein the measuring of the quantitative relaxation time (T2) comprises determining a relative amplitude of a long component of the muscle, the long component having a longer relaxation time than a short component of the muscle, (b) comparing the relative amplitude of the long component from the patient to a reference relative amplitude, wherein an increase or decrease in the relative amplitude of the long component from the patient compared to a reference relative amplitude indicates an increase or decrease, respectively, of (i) a volume of extracellular fluid space of the muscle, or (ii) an amount of extracellular fluid in the muscle, which indicates an increase or decrease, respectively, in a hydration level of the patient; and (c) determining that the fluid volume status of the patient is hypervolemic when the comparing from step (b) indicates an increase in hydration level of the patient, determining that the fluid volume status of the patient is hypovolemic when the comparing from step (b) indicates a decrease in hydration level of the patient, and determining that the fluid volume status of the patient is euvolemic when the comparing from step (b) indicates neither an increase nor a decrease in hydration level of the patient, wherein the measuring of the quantitative relaxation time (T2) is performed with a magnetic resonance device, with a single measurement.

2. The method of claim 1, wherein the reference relative amplitude is (i) calculated based on one or more characteristics of the patient, (ii) determined when the patient is euvolemic, or (iii) collected from a control patient.

3. The method of claim 1, further comprising determining, based on the relative amplitude of the long component, a ratio of extracellular fluid to intracellular fluid of the muscle.

4. The method of claim 1, wherein the measuring of the quantitative relaxation time (T2) is performed before, during, and/or after the patient is treated with dialysis.

5. The method of claim 1, wherein the measuring of the quantitative relaxation time (T2) is performed with a portable nuclear magnetic resonance sensor configured to measure the quantitative relaxation time (T2) with the single measurement.

6. The method of claim 5, wherein the portable nuclear magnetic resonance sensor is configured to measure a voxel comprising about 0.4 $cm^3$ to about 0.6 $cm^3$ of the muscle of the patient.

7. The method of claim 1, wherein the muscle of the patient is a leg muscle.

8. The method of claim 1, wherein the patient has end-stage renal disease.

9. The method of claim 1, wherein the patient has a disease or condition selected from the group consisting of congestive heart failure, renal failure, liver cirrhosis, nephrotic syndrome, brain swelling, diabetes, staphylococcal infection, nephrolithiasis, diarrhea, colitis, pyelonephritis, cystic fibrosis, Huntington's disease, rotavirus infection, herpangina, *salmonellosis*, norovirus infection, pertussis, *cryptosporidium* infection, cholera, coma, and water intoxication.

10. A method for determining a fluid volume status of a patient, wherein the patient's fluid volume includes the patient's blood volume, interstitial fluid volume, and intracellular fluid volume, and wherein the fluid volume status is hypovolemic, euvolemic, or hypervolemic, the method comprising:

(a) measuring a quantitative relaxation time (T2) of a muscle of the patient to determine a relative amplitude of a long component of the muscle, the long component having a longer relaxation time than a short component of the muscle;

(b) comparing the relative amplitude of the long component from the patient to a reference relative amplitude, wherein an increase or decrease in the relative amplitude of the long component from the patient compared to a reference relative amplitude indicates an increase or decrease, respectively, of (i) a volume of extracellular fluid space of the muscle, or (ii) an amount of extracellular fluid in the muscle, which indicates an increase or decrease, respectively, in a hydration level of the patient; and (c) determining that the fluid volume status of the patient is hypervolemic when the comparing from step (b) indicates an increase in hydration level of the patient, determining that the fluid volume status of the patient is hypovolemic when the comparing from step (b) indicates a decrease in hydration level of the patient, and determining that the fluid volume status of the patient is euvolemic when the comparing from step (b) indicates neither an increase nor a decrease in hydration level of the patient, wherein the muscle is a leg muscle, and the measuring of the quantitative relaxation time (T2) is performed with a portable nuclear magnetic resonance sensor configured to measure, with a single measurement, a voxel comprising about 0.1 $cm^3$ to about 1 $cm^3$ of the muscle.

11. A method of treatment, the method comprising:

(a) measuring, with a single measurement, a first quantitative relaxation time (T2) of a muscle of the patient to determine a relative amplitude of a long component of the muscle, the long component having a longer relaxation time than a short component of the muscle;

(b) comparing the relative amplitude of the long component from the patient to a reference relative amplitude, wherein an increase or decrease in the relative amplitude of the long component from the patient compared to a reference relative amplitude indicates an increase or decrease, respectively, of (i) a volume of extracellular fluid space of the muscle, or (ii) an amount of extracellular fluid in the muscle, which indicates an increase or decrease, respectively, in a hydration level of the patient;

(c) determining a first fluid volume status of the patient, wherein the patient's fluid volume includes the patient's blood volume, interstitial fluid volume, and intracellular fluid volume, by determining that the first fluid volume status of the patient is hypervolemic when the comparing from step (b) indicates an increase in hydration level of the patient, determining that the first fluid volume status of the patient is hypovolemic when the comparing from step (b) indicates a decrease in hydration level of the patient, and determining that the first fluid volume status of the patient is euvolemic when the comparing from step (b) indicates neither an increase nor a decrease in hydration level of the patient; and (d) administering to the patient a first treatment comprising a fluid reduction treatment or a hydration treatment if the first fluid volume status of the patient is hypervolemic or hypovolemic, respectively.

12. The method of claim 11, further comprising:

determining a second fluid volume status of the patient after the administering of the first treatment by measuring a second quantitative relaxation time (T2) of a muscle of the patient; and administering to the patient a second treatment comprising a fluid reduction treatment or a hydration treatment if the second fluid volume status of the patient is hypervolemic or hypovolemic, respectively.

13. The method of claim 11, wherein the fluid reduction treatment comprises hemodialysis.

14. The method of claim 11, wherein the measuring of the quantitative relaxation time (T2) is performed with a portable nuclear magnetic resonance sensor configured to measure the quantitative relaxation time (T2) with the single measurement.

15. The method of claim 14, wherein the portable nuclear magnetic resonance sensor is configured to measure a voxel comprising about 0.4 $cm^3$ to about 0.6 $cm^3$ of the muscle of the patient.

16. The method of claim 11, wherein the patient has end-stage renal disease.

17. The method of claim 11, wherein the patient has a disease or condition selected from the group consisting of congestive heart failure, renal failure, liver cirrhosis, nephrotic syndrome, brain swelling, diabetes, staphylococcal infection, nephrolithiasis, diarrhea, colitis, pyelonephritis, cystic fibrosis, Huntington's disease, rotavirus infection, herpangina, *salmonellosis*, norovirus infection, pertussis, *cryptosporidium* infection, cholera, coma, and water intoxication.

18. The method of claim 11, wherein the muscle of the patient is a leg muscle.

* * * * *